(12) United States Patent
Beumer et al.

(10) Patent No.: US 8,394,500 B2
(45) Date of Patent: Mar. 12, 2013

(54) COMPOSITIONS BASED ON HYPERBRANCHED CONDENSATION POLYMERS AND NOVEL HYPERBRANCHED CONDENSATION POLYMERS

(75) Inventors: Raphael Beumer, Loerrach (DE); Franciscus Johannes M. Derks, DL Heythusysen (NL)

(73) Assignee: DSM IP Assets B.V., Heerlen (NL)

( * ) Notice: Subject to any disclaimer, the term of this patent is extended or adjusted under 35 U.S.C. 154(b) by 862 days.

(21) Appl. No.: 12/304,654

(22) PCT Filed: Jun. 15, 2007

(86) PCT No.: PCT/EP2007/005290
§ 371 (c)(1),
(2), (4) Date: May 26, 2009

(87) PCT Pub. No.: WO2007/144189
PCT Pub. Date: Dec. 21, 2007

(65) Prior Publication Data
US 2010/0069601 A1 Mar. 18, 2010

(30) Foreign Application Priority Data
Jun. 16, 2006 (EP) .................................. 06012378

(51) Int. Cl.
*C08L 77/12* (2006.01)
(52) U.S. Cl. .................. 428/423.1; 428/474.4
(58) Field of Classification Search ............... 428/423.1
See application file for complete search history.

(56) References Cited

U.S. PATENT DOCUMENTS

| 3,378,494 A | 4/1968 | Berger |
| 4,263,153 A * | 4/1981 | O'Halloran et al. .......... 508/227 |
| 6,645,636 B2 * | 11/2003 | Van Benthem ............ 428/423.1 |
| 6,654,636 B1 * | 11/2003 | Dev et al. ........................ 604/21 |
| 2005/0014893 A1 * | 1/2005 | Braun et al. .................. 524/801 |
| 2005/0090611 A1 | 4/2005 | Huffer et al. |

FOREIGN PATENT DOCUMENTS

| GB | 1 053 356 | 8/1965 |
| GB | 2 055 804 | 3/1981 |
| WO | 00/56804 | 9/2000 |
| WO | 00/58388 | 10/2000 |
| WO | WO 0058388 A1 * | 10/2000 |
| WO | 02/102928 | 12/2002 |

OTHER PUBLICATIONS

International Search Report for PCT/EP2007/005290, mailed Jan. 1, 2008.
Written Opinion for PCT/EP2007/005290, mailed Jan. 1, 2008.

* cited by examiner

*Primary Examiner* — James J Seidleck
*Assistant Examiner* — Peter A Salamon
(74) *Attorney, Agent, or Firm* — Nixon & Vanderhye P.C.

(57) ABSTRACT

The invention relates to personal care, home care and fabric care compositions based on hyperbranched condensation polymers having in the polymer backbone at least one unit comprising an amide bond attached to a trismethylene-aminomethane group and to novel hyperbranched condensation polymers.

22 Claims, No Drawings

COMPOSITIONS BASED ON HYPERBRANCHED CONDENSATION POLYMERS AND NOVEL HYPERBRANCHED CONDENSATION POLYMERS

This application is the U.S. national phase of International Application No. PCT/EP2007/005290, filed 15 Jun. 2007, which designated the U.S. and claims priority to Europe Application No. 06012378.3 filed 16 Jun. 2006, the entire contents of each of which are hereby incorporated by reference.

The invention relates to personal care, home care and fabric care compositions based on hyperbranched condensation polymers and to novel hyperbranched condensation polymers. More particularly, the invention relates, in one aspect, to personal care and home care compositions based on hyperbranched condensation polymers having in the polymer backbone at least one unit comprising an amide bond attached to a trismethylene-aminomethane group (hereinafter referred to also as condensation polymers). Specifically, such condensation polymers comprise at least two groups of the general formula (I)

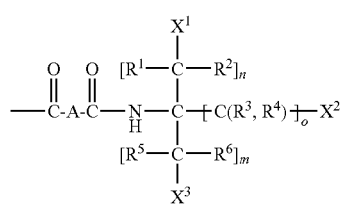

Formula (I)

wherein
the free bond extends to the polymer backbone;
A is an, optionally substituted, ($C_6$-$C_{24}$) aryldiradical or an, optionally substituted, ($C_2$-$C_{24}$) (cyclo)alkyldiradical,
$R^1$ to $R^6$ are, independently of each other, hydrogen, $C_{1-20}$-alkyl, $C_{3-7}$-cycloalkyl or $C_{6-10}$-aryl;
$X^1$, $X^2$ and $X^3$ are, independently of each other, hydrogen, hydroxy, $C_{1-20}$-alkyl, $C_{1-20}$-alkoxy, $C_{3-7}$-cycloalkyl, $C_{6-10}$-aryl or a group —O—CO—$R^7$, —O—CO-A-CO—N($R^8$, $R^9$), —O—CO-A-CO—O$R^{10}$, or —NHet;
$R^7$ is $C_{1-20}$-alkyl, $C_{3-7}$-cycloalkyl, $C_{6-10}$-aryl, or a radical of a polymer or an oligomer;
$R^8$ and $R^9$ are, independently of each other, ($C_{1-20}$)-alkyl or ($C_{6-10}$)-aryl groups; or ($C_{1-20}$)-alkyl or ($C_{6-10}$)-aryl groups substituted by a group containing at least one hetero atom or
$R^8$ and $R^9$ together with the nitrogen atom to which they are attached form a 5 or 6 membered ring wherein optionally one or several C-atoms are replaced by —NH, —N—($C_{1-20}$)-alkyl, —N-aryl, —O— or —S—;
$R^{10}$ is $C_{1-20}$-alkyl, $C_{3-7}$-cycloalkyl, or $C_{6-10}$-aryl or a radical of a polymer or an oligomer;
NHet is, independently of each other, a mono-, bi- or multicyclic nitrogen containing heterocyclyl group attached via a nitrogen atom to the polymer which may be aromatic or partly or completely hydrogenated and may contain additional heteroatoms such as nitrogen, oxygen or sulfur and which may optionally be substituted; and
n, m, o are, independently of each other, an integer of 1 to 4, preferably n, m and o are equal to 1.
provided that no more than one of $X^1$, $X^2$ and $X^3$ is hydrogen, $C_{1-20}$-alkyl, $C_{3-7}$-cycloalkyl, or $C_{6-10}$-aryl;
and wherein nitrogen containing groups may be quaternized or protonated.

The condensation polymers as defined above may be used in personal care products and home care products to achieve product characteristics which are typically desired in such products, such as exhibiting low stickiness, lack of powdering or flaking, preferably being clear, transparent and glossy.

Typical personal care and home care products according to the invention are skin-care preparations, bath and shower preparations, liquid soaps, bar soaps, preparations containing scents, fragrances and odorant ingredients, hair-care preparations; dentifrice, deodorizing and antiperspirant preparations, decorative preparations, and light protecting preparations.

Of particular interest in context with the present invention are hair care preparations, e.g., conditioners, shampoos, styling gels and mousses, and hair fixating sprays wherein the polymers defined above may find use as conditioning agents, strengthening agents, film forming agents, surfactants, antistatic agents, moisturizers, emulsifiers or hair styling agents. In hair care preparation for example film forming polymers are used e.g. as conditioning agent in order to improve the combability, the shine and the visible appearance of the hair as well as to give the hair antistatic properties.

Personal care products such as hair care preparation should additionally fulfill a variety of requirements in regard of their performance such as providing a fine spray pattern, a good film formation, a good holding power, a high level of style retention, a prolonged curl retention, an improved combability, and should be easy to remove upon washing the hair with shampoo or soap.

The polymers as defined above are suitable for the incorporation into personal care products or home care products possess properties desired for the manufacture of such products, viz., heat stability, good solubility, compatibility with cosmetic bases, pH stability in the range of 4 to 9, processability into a variety of products, compatibility with other ingredients and with the packaging materials, are of neutral color and odor and have a low volatility.

In one embodiment, the compositions of the present invention comprise condensation polymers wherein at least one group of the general formula (I) is present wherein $R^1$ to $R^6$ are hydrogen.

In another embodiment, the compositions of the present invention comprise condensation polymers wherein one of $X^1$, $X^2$ and $X^3$ is methyl.

In still another embodiment, the compositions of the present invention comprise condensation polymers wherein at least one of $X^1$, $X^2$ and $X^3$ is hydroxy, or —O—CO—$R^7$, or —O—CO-A-CO—N($R^8$,$R^9$), or —O—CO-A-CO—O$R^{10}$, or —NHet.

In all embodiments of the invention:
the term $C_{6-10}$-aryl denotes moieties of aromatic hydrocarbons having 6 to 10 carbon atoms, particularly phenyl, tolyl, xylyl, and naphthyl.
the term ($C_{6-24}$) aryldiradical denotes a divalent moiety of an aromatic or hydroaromatic hydrocarbon having 6 to 24 carbon atoms, particularly 1,2-phenylene, 1,3-phenylene, 1,4-phenylene, or naphthylene, tetrahydro- or hexahydronaphthylene or norbornene which may be substituted, e.g., by alkyl or alkenyl.
the term $C_{1-20}$-alkyl denotes straight or branched alkyl groups having up to 20 carbon atoms, particularly methyl, ethyl, propyl, isopropyl, n-butyl, sec-butyl and tert-butyl. The term $C_{3-7}$-cycloalkyl denotes cycloalkyl groups having 3 to 7 carbon atoms, particularly cyclopropyl, cyclobutyl, cyclopentyl and cyclohexyl. The $C_{1-20}$-alkyl groups may be saturated or unsaturated.
the term ($C_2$-$C_{24}$) (cyclo)alkyldiracical denotes a divalent moiety of a saturated straight or branched (cyclo)hydrocarbon having 2 to 24 carbon atoms, which may be substituted by $C_1$-$C_{20}$ alkyl or by $C_2$-$C_{20}$ alkenyl.

In all embodiments of the invention A may be saturated or unsaturated. A may optionally be substituted, preferably with a $C_1$-$C_{20}$ alkyl or by $C_2$-$C_{20}$ alkenyl group such as methyl, octenyl, nonenyl, decenyl, undecenyl or dodecenyl.

Suitable choices for A are ethylene, propylene, (alkyl-)1,2-ethylene, where the alkyl is defined as above, (methyl-)1,2-ethylidene, 1,3-propylene, (methyl-)1,2-cyclohexyl, (methyl-)1,2-phenylene, 1,3-phenylene, 1,4-phenylene, 2,3-norbornyl, 2,3-norbornen-5-yl, tetrahydro-1,2-phenylene or (methyl-)1,2-cyclohex-4-enyl radical. Preferably, A is ethylene, propylene or 1,2-cyclohexyl.

$R^7$ can be chosen from, for example, a saturated or unsaturated ($C_1$-$C_{20}$) alkyl or $C_{3-7}$-cycloalkyl, $C_{6-10}$-aryl, a polymer or an oligomer. In all embodiments of the invention $R^7$ is preferably chosen from ($C_1$-$C_{20}$) alkyl groups or a radical of a polymer or an oligomer. Examples of suitable polymers are polyesters, polyethers, poly(capro)lactones, polyethyleneoxides, polypropyleneoxide methyl ether, polytetrahydrofuranes, polysilicones or fluoro polymers or oligomers.

$R^7$ can be substituted with for example ester groups, ether groups, amide groups and alcohol groups. The condensation polymer may comprise the same or different $R^7$ groups.

Preferably, the $R^7$ is chosen from phenyl, methyl, ethyl, propyl, isopropyl, n-butyl, sec-butyl, tert-butyl or 2-ethylhexyl or groups derived from natural fatty acids such as sojabean fatty acid, coconut fatty acid or sunflower fatty acid. If $R^7$ is a radical of a polymer or an oligomer it is preferably selected from polyethyleneoxide, polypropyleneoxide or polytetrahydrofurane.

If $R^8$ and $R^9$ are ($C_1$-$C_{20}$) alkyl groups they may be substituted by substituents optionally comprising one or more heteroatoms. More preferably, $R^8$ and $R^9$ are linear $C_2$-, $C_3$- or $C_6$-alkyl groups wherein one or several C-atoms may substituted by substituents optionally comprising nitrogen, oxygen or sulfur.

Thus, $R^8$ and $R^9$ may be substituted by a group selected from the group consisting of alcohol, ether, ester, cyanide, carbonate, urethane, urea, amide, imide, amine, imine or imidazole, oxime, sulfide, thiol, thiourea, sulfone, sulfoxide, sulfate, phosphate, phosphine, phosphinoxide, silane, silicone, silicate, fluoro, chloro, bromo or iodo groups. Examples of such groups —N($R^8$,$R^9$) are dimethylamino, diethylamino, dibutylamino, dioctylamino, ethylhexyl-methyl(or ethyl) amino, di-(2-ethylhexyl)amino, distearylamino, diallylamino, dicrotylamino, N-methyl(or ethyl)allylamino, bis(dimethyl(or ethyl)aminopropyl)amino, bis(dimethyl (or ethyl)aminohexyl)amino, bis(dimethyl(or ethyl)aminoethyl) amino, bis(trimethylsilylpropyl)amino, bis(trimethyl(or triethyl)ethoxysilylpropyl)amino, bis(perfluorooctyl)amino, bis(perfluorooctyl-methyl(or ethyl)amino, bis(methoxyethyl)amino, N-methyl(or ethyl)methoxyethylamino, bis(methoxy-2-propyl)amino, bis(maleimidohexyl)amino, bis(octenylsuccinimidopropyl)amino, bis(hexahydrophthalimidohexyl)amino, difurfurylamino, dicyano(m)ethylamino, bis(diphenylphosphinoethyl)amino.

Preferably, $R^8$ and $R^9$ are di-($C_{1-20}$-alkyl)amino-$C_{1-20}$-alkyl groups such as N,N-dimethylaminopropyl.

Examples of groups —N($R^8$,$R^9$) wherein $R^8$ and $R^9$ together form an N-heterocyclic ring are morpholino, thiormorpholino, piperidino, pyrrolidino, N-methyl piperazino, (2-phenyl)oxazolidino, thiazolidino, piperazino, 2,2,6,6-tetramethylpiperidino, and di(benzyl)amino.

Preferably, the N-heterocyclic ring is an N-methyl piperazine or a morpholino group.

In all embodiments of the invention —$OR^{10}$ is derived from a saturated or unsaturated hydroxy functional monomer, oligomer or polymer, wherein $R^{10}$ can be aryl, alkyl, cycloalkyl or the radical of polyethyleneoxide, polypropyleneoxide, polytetrahydrofurane, polysilicones, fluoro polymers or a nylon oligomer. Preferably $R^{10}$ is an, optionally substituted, ($C_1$-$C_{26}$) alkyl group or a radical of polyethyleneoxide. Preferably, the alkyl group is selected from the group of phenyl, methyl, ethyl, propyl, isopropyl, n-butyl, sec-butyl, tert-butyl or 2-ethylhexyl or groups derived from natural fatty acids such as sojabean fatty acid, coconut fatty acid or sunflower fatty acid. If $R^{10}$ is a radial of a polymer or an oligomer it is preferably selected from polyethyleneoxide, polyethyleneoxide methyl ether, polypropyleneoxide, polypropyleneoxide methyl ether and/or polytetrahydrofurane in particular from polyethyleneoxide methyl ether, polypropyleneoxide methyl ether and/or polytetrahydrofurane.

Examples of heterocyclic compounds from which the moiety —NHet may be derived are those having a labile hydrogen atom selected from substituted or unsubstituted mono-, bi- or multicyclic heterocycles such as pyrrol, pyrazole, imidazole, pyrazolon, indole, benzimidazole, isatin, oxazolidine, 2-oxazolidone, oxindole, triazole such as 1,2,3-triazole or 1,2,4-triazole, tetrazole, pentazole, pyridazinone, barbituric acid, nucleic acids and such as cytosine, uracil, thymine or thiouracil, dioxopiperazine, chinazolinone, phthalazinone, purine, xanthin, pterin, cyclic lactames such as gamma-butyrolactam or alpha-piperidone or bicyclic amidines and derivatives thereof. Optionally such heterocyclic compounds may be completely or partly hydrogenated and may be substituted. Suitable substituents, one or several, may be selected independently from the group of alcohol, ether, ester, cyanide, amide, amine, imine, oxime, sulfide, thiol, sulfone, sulfoxide, sulfate, phosphate, phosphine, phosphinoxide, silane, silicone, silicate, fluoro, chloro, bromo or iodo groups or carbonyl groups. Most preferred are, optionally substituted, imidazole, benzimidazole, 1,2,4-triazole and hydantoin.

Condensation polymers comprising at least a group of the general formula (I) as defined earlier wherein $X^1$, $X^2$ and $X^3$ are, independently of each other, a group —O—CO-A-CO—N($R^8$,$R^9$), —O—CO-A-CO—$OR^{10}$, or —NHet; and $R^1$ to $R^6$, $R^8$, $R^9$, and —NHet are as defined earlier, and wherein nitrogen containing groups may be quaternized, are novel and, as such, are also an object of the present invention.

The condensation polymers used in the compositions of the present invention may have, typically, a weight average molecular mass between 600 g/mol to 50,000 g/mol, more preferably between 800 g/mol and 25,000 g/mol, respectively, a number average molecular mass of about 500 g/mol and 15,000 g/mol, more preferably between 700 g/mol and 4,000 g/mol.

The condensation polymers used in the compositions of the present invention may be prepared by polycondensation of a compound of the general formula (II)

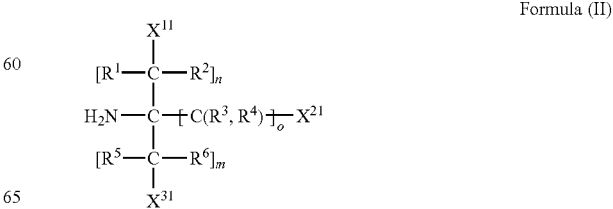

Formula (II)

wherein $R^1$ to $R^6$ and n, m and o are as defined earlier in formula (I) and $X^{11}$, $X^{21}$ and $X^{31}$ have the same meaning as $X^1$, $X^2$ and $X^3$ in formula (I) as defined earlier, provided that at least one of $X^{11}$, $X^{21}$ and $X^{31}$ is hydroxy, and further provided that no more than one of $X^{11}$, $X^{21}$ and $X^{31}$ is hydrogen, $C_{1-20}$-alkyl, $C_{3-7}$-cycloalkyl, or $C_{6-10}$-aryl;

with a dicarboxylic acid of the general formula $$A(COOH)_2 \quad (III)$$

or the cyclic anhydride thereof wherein A has the same meaning as in formula (I) as defined earlier; and, optionally, an acid of the general formula $$R^7COOH \quad (IV)$$

and/or a dialkylamine of the general formula $$HN(R^8R^9) \quad (V),$$

and/or an alcohol of the general formula $$R^{10}OH \quad (VI)$$

and/or a heterocycle of the general formula $$H\text{—NHet} \quad (VII)$$

wherein $R^7$, $R^8$, $R^9$, $R^{10}$ and —NHet have the same meaning as in formula (I) defined earlier, Optionally, at least one additional alkanolamines according to formula (VIII):

$$H-N\begin{pmatrix}R^{12}\\|\\C\\|\\R^{13}\end{pmatrix}_p \begin{matrix}R^{14}\\|\\C-OH\\|\\H\end{matrix} \quad \text{Formula VIII}$$
$\quad\;\;|$
$\quad\;\;Y$ in which:
Y is $$-\begin{pmatrix}R^{15}\\|\\C\\|\\R^{16}\end{pmatrix}_q \begin{matrix}R^{17}\\|\\C-OH\\|\\H\end{matrix}$$

or a linear, branched or cyclic ($C_1$-$C_{20}$) alkyl group;
$R^{12}$, $R^{13}$, $R^{14}$, $R^{15}$, $R^{16}$ and $R^{17}$ are, independently of each other a hydrogen atom, ($C_6$-$C_{10}$) aryl groups, ($C_1$-$C_8$) alkyl groups or $CH_2OH$
and p and q are an integer from 1 to 4, preferably, p and q are 1
may be added to the polycondensation process in order adjust the degree of branching of the condensation polymer.

Optionally, quaternization or protonation of one or more nitrogen containing groups in the condensation polymer may be performed after the polycondensation reaction.

The reaction can be carried out in a one-step procedure at room temperature or at an elevated temperature, preferably between about 20° C. and about 120° C., to form an amide bond between the amino group of the compound of formula (II) and the carboxy group of the dicarboxylic acid or the anhydride thereof after which, at an elevated temperature, preferably between 120° C. and 250° C., a polyesteramide is obtained through polycondensation with water being removed, preferably through distillation. The one-step procedure can take place with or without a solvent. Suitable solvents are organic solvents, such as methyl-isobutylketone, butylacetate, toluene or xylene. The removal of water through distillation can take place at either reduced or elevated pressure, such as at a pressure higher than $1.10^5$ Pa, in a vacuum ($<1.10^5$ Pa) or azeotropically.

Examples of compounds of formula (II) are tris-hydroxymethyl-aminomethane and 2-amino-2-ethyl-1,3-propanediol.

Examples of cyclic anhydrides of dicarboxylic acids of the formula $A(COOH)_2$ are phthalic anhydride, tetrahydrophthalic anhydride, naphtalenic dicarboxylic anhydride, hexahydrophthalic anhydride, 5-norbornene-2,3-dicarboxylic anhydride, norbornene-2,3-dicarboxylic anhydride, succinic anhydride, 2-octene-1-yl-succinic anhydride, 2-nonene-1-yl-succinic anhydride, 2-decene-1-yl-succinic anhydride, 2-undecene-1-yl-succinic anhydride 2-dodecene-1-yl-succinic anhydride, maleic anhydride, (methyl)succinic anhydride, glutaric anhydride, 4-methylphthalic anhydride, 4-methylhexahydrophthalic anhydride, 4-methyltetrahydrophthalic anhydride, maleinised poly-isobutylene, maleinised polybutadiene and the maleinised alkylester of an unsaturated fatty acid.

Examples of carboxylic acids (IV) are monomeric, oligomeric or polymeric monofunctional carboxylic acid. Suitable carboxylic acids are, for example, saturated aliphatic ($C_1$-$C_{20}$) acids, unsaturated ($C_1$-$C_{20}$) fatty acids, aromatic acids and [alpha], [beta]-unsaturated acids or natural fatty acids. Examples of suitable [alpha],[beta]-unsaturated acids are (meth)acrylic acid, crotonic acid and monoesters or monoamides of itaconic acid, maleic acid, 12-hydroxystearic acid, polyether carboxylic acid, and fumaric acid. Suitable saturated aliphatic acids are for example acetic acid, propionic acid, butyric acid, 2-ethyl hexanoic acid, laurylic acid and stearic acid. Suitable aromatic acid are for example benzoic acid and tertiary butyl benzoic acid. Examples of natural fatty acids comprises sunflower fatty acid, coconut fatty acid or sojabean fatty acid Examples of dialkylamines (V) of the formula $HN(R^8R^9)$ are dimethylamine, diethylamine, dibutylamine, dioctylamine, ethylhexyl-methyl(or ethyl)amine, di-(2-ethylhexyl) amine, distearylamine, diallylamine, dicrotylamine, N-methyl(or ethyl)allylamine, bis(aminopropyl)amine, bis (aminohexyl)amine, N-methyl(or ethyl)-aminopropylamine, bis(dimethyl(or ethyl)aminopropyl)amine, bis(dimethyl (or ethyl)aminohexyl)amine, bis(dimethyl(or ethyl)aminoethyl) amine, bis(trimethylsilylpropyl)amine, bis(trimethyl(or triethyl)ethoxysilylpropyl)amine, bis(perfluorooctyl)amine, bis(perfluorooctyl-methyl(or ethyl)amine, bis(methoxyethyl)amine, N-methyl(or ethyl)methoxyethylamine, bis(methoxy-2-propyl)amine, bis(maleimidohexyl)amine, bis(octenylsuccinimidopropyl)amine, bis (hexahydrophthalimidohexyl)amine, difurfurylamine, dicyano(m)ethylamine, bis(diphenylphosphinoethyl)amine, morpholine, thiormorpholine, piperidine, pyrrolidino, (2-phenyl)oxazolidine, thiazolidine, piperazine, N-methylpiperazine, oxazolidine, 2,2,6,6,tetramethylpiperidine, and dibenzylamine and derivatives thereof.

Examples of alcohols (VI) are e.g methanol, ethanol, propanol, butanol, tert-butanol, 2-ethylhexanol, fatty alcohols such as cetearyl alcohol, cetyl alcohol, stearyl alcohol, Polychol 5 and hydroxy functional polymers like polyethyleneoxide, polypropyleneoxide, polytetrahydrofurane, polysilicones, fluoro polymers or a nylon oligomer. Preferably polyethyleneoxide monomethylether.

Examples of heterocyclic compounds of formula (VII) above are those particularly disclosed above as providing the moiety —NHet.

Examples of alkanolamines of formula VIII are monoalkanolamines or dialkanolamines. Examples of suitable mono-β-alkanolamines include ethanolamine, 1-(m)ethyl ethanolamine, n-butyl ethanolamine, 1-(m)ethyl isopropanolamine, isobutanolamine, β-cyclohexanolamine, n-butyl isopropanolamine and n-propanolamine.

Examples of suitable di-β-alkanolamines are diethanolamine, 3-amino-1,2-propanediol, 2-amino-1,3-propanediol, diisobutanolamine (bis-2-hydroxy-1-butyl)amine), di-β-cyclohexanolamine and diisopropanolamine (bis-2-hydroxy-1-propyl)amine).

In addition to hydroxy, —O—CO—$R^7$, —O—CO-A-CO—N($R^8$,$R^9$), or —O—CO-A-CO—$OR^{10}$, or —NHet end-groups the polymer may also contain carboxyl groups and/or β-hydroxyalkylamide groups. Carboxyl groups can be present in, for example, amounts of between 0.01 and 2.0 mg equivalent/gram of polymer. β-Hydroxyalkylamide groups may be present in amounts of between 0.01 and 5.0 mg equivalent/gram polymer. The amount of p-hydroxyalkylamide groups can be controlled via the ratio of the compound of formula (II) and optionally formula (VIII) and the reactants of formula (III), (IV), (V), (VI) and (VII) and via the degree of conversion. If hydroxy groups are present in the condensation polymer they may in a subsequent step react with compounds containing one or more groups that can react with hydroxyl groups, such as for example carboxyl acids, carboxylic anhydrides, isocyanates, activated esters or carboxylic halides leading to entirely or partly modified polymers.

Thus the invention also relates to entirely or partly modified polymers. The modification can for example take place via a reaction between the condensation polymer comprising a group of formula (I) wherein at least one $X^1$, $X^2$ and/or $X^3$ is a hydroxy group with a monomer, oligomer or polymer containing reactive groups. Examples of suitable reactive groups include carboxyl groups, carboxylic esters, carboxylic anhydrides, epoxy groups, alkoxysilane groups, isocyanate groups, acid chloride groups, epoxychlorohydrine groups, amine groups, phenolic groups, methylolated amide groups and combinations hereof. Preferably the monomer, oligomer or polymer contains only one group that can react with hydroxyl group, as a result of which no crosslinking takes place during the modification.

The degree of branching and the functionality of the polymer are dependent on the starting materials and the molecular weight of the polymer. A molecular weight higher than 2,000 and the use of di- and/or trialkanolamines generally lead to highly branched structures with a functionality of ≧6.

Preferably, the average number of end groups $X^1$, $X^2$ and/or $X^3$ per molecule of condensation polymer is between 2 and 250, more preferably between 3 and 50.

The optionally one or several nitrogen atoms of the condensation polymer which are present in quaternized or protonated forms may be prepared by reaction of the nitrogen atoms of the non-quaternized condensation polymer with customary quaternizing or protonating agents according to standard procedures as e.g. described in Jerry March, 'Advanced organic chemistry, $4^{th}$ edition, Wiley-Interscience p. 411ff.

Suitable quaternization reagents are e.g. alkyl or aryl halides such as Me iodide, Me chloride, ethyl iodide, phenyl iodide, allyl chloride, vinyl chloride; sulfates such as dimethylsulfate, diethylsulfate; glycidyl ethers and esters such as allyl glycidyl ester and glycidyl methacrylate without being limited thereto. Suitable quaternization agents to obtain the betaine group are chloro acetic acid and (meth-)acrylic acid. The quaternization procedure can take place with or without a solvent. Suitable solvents are water or an organic solvent, such as e.g. acetonitrile. The quaternized condensation polymer can be used as solution in the respective solvent or the solvent can be evaporated to yield a dried condensation polymer.

Preferably, the nitrogen atoms are quaternized with methyl and/or ethyl groups.

Suitable protonation agents are e.g. inorganic acids such as HCl; $H_3PO_4$; $H_2SO_4$ and other cosmetically acceptable acids like acetic acid, tartaric acid, fumaric acid, lactic acid, malic acid, succinic acid, and mixtures thereof. Preferably, the acid is selected from the group consisting of acetic acid, tartaric acid, hydrochloric acid, fumaric acid, and mixtures thereof; The protonation procedure can take place with or without a solvent. Suitable solvents are water or an organic solvent, such as e.g. acetonitrile. The protonated condensation polymer can be used as solution in the respective solvent or the solvent can be evaporated to yield a dried condensation polymer.

Dependent on the desired degree of the quaternization, respectively protonation, the amount of quaternization or protonation agent to nitrogen atoms has to be adjusted accordingly.

The preferred degree of quaternization, respectively protonation, of the nitrogen atoms of the condensation polymer is between 20 and 100%, more preferred between 50 and 100%, most preferred 80 and 100%.

Another embodiment of the invention is a personal care product or household product comprising an effective amount of a condensation polymer.

The term "effective amount" means generally at least a concentration of 0.01% by weight based on the total formulation. Preferably, a concentration of 0.01 to 20 wt. %, most preferred of 0.05 to 10 wt. % is used.

In a further embodiment the invention relates to a personal care product comprising a condensation polymer as outlined above and additional cosmetic or dermatological adjuvants and/or additives.

Preferably, the personal care product according to the invention is selected from skin-care preparations; bath and shower preparations; liquid soaps; bar soaps; preparations containing scents, fragrances and odorant ingredients; hair-care preparations; dentifrices; deodorizing and antiperspirant preparations; decorative preparations; light protecting preparations and preparations containing active ingredients.

Preferred personal care products according to the invention are hair care preparations comprising additional additives and adjuvants used in hair care.

In a further embodiment the invention relates to a method of treating hair in which a personal care product such as a hair care preparation is applied to the hair.

In another embodiment the invention relates to the use of a condensation polymer as defined above as conditioning agent, strengthening agent, film forming agent, surfactant, anti-static agent, moisturizer, emulsifier or hair styling agent.

The personal care products according to the invention comprise additional cosmetic or dermatological adjuvants and/or additives (cosmetic carrier) which are preferable selected from
  1.) Water
  2.) Water soluble organic solvents, preferably $C_1$-$C_4$-Alkanols
  3.) Oils, fatty substances, waxes
  4.) Various esters different to 3) of $C_6$-$C_{30}$ monocarbonic acids with one-, two, or three valent alcohols
  5.) Saturated acyclic and cyclic hydrocarbons
  6.) Fatty acids
  7.) Fatty alcohols
  8.) Silicone oils
and mixtures thereof.

The personal care products or household products according to the invention can contain further adjuvants and additives such as preservatives/antioxidants, fatty substances/oils, water, organic solvents, silicones, thickeners, softeners, emulsifiers, additional screening agents, antifoaming agents, moisturizers, fragrances, surfactants, fillers, sequestering agents, anionic, cationic, nonionic or amphoteric polymers or mixtures thereof, propellants, acidifying or basifying agents, dyes, colorants, pigments or nanopigments, light stabilizers, insect repellants, skin tanning agents, skin whitening agents, antibacterial agents, preservatives or any other ingredients usually formulated into cosmetics. The necessary amounts of the cosmetic and dermatological adjuvants and additives can, based on the desired product, easily be chosen by a skilled artisan in this field and will be illustrated in the examples, without being limited hereto.

Light Screening Agents

Additional screening agents are advantageously selected from UV-A, UV-B, UV-C and/or broadband filters. Examples of UV-B or broad spectrum screening agents, i.e. substances having absorption maximums between about 290 nm and 340 nm may be organic or inorganic compounds. Organic UV-B or broadband screening agents are e.g. acrylates such as 2-ethylhexyl 2-cyano-3,3-diphenylacrylate (octocrylene, PARSOL® 340), ethyl 2-cyano-3,3-diphenylacrylate and the like; camphor derivatives such as 4-methyl benzylidene camphor (PARSOL® 5000), 3-benzylidene camphor, camphor benzalkonium methosulfate, polyacrylamidomethyl benzylidene camphor, sulfo benzylidene camphor, sulphomethyl benzylidene camphor, therephthalidene dicamphor sulfonic acid and the like; cinnamate derivatives such as ethylhexyl methoxycinnamate (PARSOL® MCX), ethoxyethyl methoxycinnamate, diethanolamine methoxycinnamate (PARSOL® Hydro), isoamyl methoxycinnamate and the like as well as cinnamic acid derivatives bond to siloxanes; p-aminobenzoic acid derivatives, such as p-aminobenzoic acid, 2-ethylhexyl p-dimethylaminobenzoate, N-oxypropylenated ethyl p-aminobenzoate, glyceryl p-aminobenzoate; benzophenones such as benzophenone-3, benzophenone-4, 2,2', 4,4'-tetrahydroxy-benzophenone, 2,2'-dihydroxy-4,4'-dimethoxybenzophenone and the like; esters of benzalmalonic acid such as di-(2-ethylhexyl) 4-methoxybenzalmalonate; esters of 2-(4-ethoxy-anilinomethylene)propandioic acid such as 2-(4-ethoxy anilinomethylene) propandioic acid diethyl ester as described in the European Patent Publication EP 0895 776; organosiloxane compounds containing benzmalonate groups as described in the European Patent Publications EP 0358584 B1, EP 0538431 B1 and EP 0709080 A1 such as PARSOL® SLX; drometrizole trisiloxane (Mexoryl XL); imidazole derivatives such as e.g. 2-phenyl benzimidazole sulfonic acid and its salts (PARSOL®HS). Salts of 2-phenyl benzimidazole sulfonic acid are e.g. alkali salts such as sodium- or potassium salts, ammonium salts, morpholine salts, salts of primary, sec. and tert. amines like monoethanolamine salts, diethanolamine salts and the like; salicylate derivatives such as isopropylbenzyl salicylate, benzyl salicylate, butyl salicylate, ethylhexyl salicylate (PARSOL® EHS, Neo Heliopan OS), isooctyl salicylate or homomethyl salicylate (homosalate, PARSOL® HMS, Neo Heliopan HMS) and the like; triazine derivatives such as ethylhexyl triazone (Uvinul T-150), diethylhexyl butamido triazone (Uvasorb HEB) and the like. Encapsulated UV-filters such as encapsulated ethylhexyl methoxycinnamate (Eusolex UV-pearls) or microcapsules loaded with UV-filters as e.g. disclosed in EP 1471995 and the like; Inorganic compounds are pigments such as microparticulated $TiO_2$, and the like. The term "microparticulated" refers to a particle size from about 5 nm to about 200 nm, particularly from about 15 nm to about 100 nm. The $TiO_2$ particles may also be coated by metal oxides such as e.g. aluminum or zirconium oxides or by organic coatings such as e.g. polyols, methicone, aluminum stearate, alkyl silane. Such coatings are well known in the art.

Examples of broad spectrum or UV A screening agents i.e. substances having absorption maximums between about 320 nm and 400 nm may be organic or inorganic compounds e.g. dibenzoylmethane derivatives such as 4-tert.-butyl-4'-methoxydibenzoyl-methane (PARSOL® 1789), dimethoxydibenzoylmethane, isopropyldibenzoylmethane and the like; benzotriazole derivatives such as 2,2'-methylene-bis-(6-(2H-benzotriazole-2-yl)-4-(1,1,3,3,-tetramethylbutyl)-phenol (Tinosorb M) and the like; bis-ethylhexyloxyphenol methoxyphenyl triazine (Tinosorb S) and the like; phenylene-1,4-bis-benzimidazolesulfonic acids or salts such as 2,2-(1,4-phenylene)bis-(1H-benzimidazole-4,6-disulfonic acid) (Neoheliopan AP); amino substituted hydroxybenzophenones such as 2-(4-diethylamino-2-hydroxy-benzoyl)-benzoic acid hexylester (Uvinul A plus) as described in the European Patent Publication EP 1046391; ionic UV-A filters as described in the International Patent Publication WO2005080341 A1; pigments such as microparticulated ZnO or $TiO_2$ and the like. The term "microparticulated" refers to a particle size from about 5 nm to about 200 nm, particularly from about 15 nm to about 100 nm. The particles may also be coated by other metal oxides such as e.g. aluminum or zirconium oxides or by organic coatings such as e.g. polyols, methicone, aluminum stearate, alkyl silane. Such coatings are well known in the art.

As dibenzoylmethane derivatives have limited photostability it may be desirable to photostabilize these UV-A screening agents. Thus, the term "conventional UV-A screening agent" also refers to dibenzoylmethane derivatives such as e.g. PARSOL® 1789 stabilized by, e.g. 3,3-diphenylacrylate derivatives as described in the European Patent Publications EP 0 514 491 B1 and EP 0 780 119 A1; benzylidene camphor derivatives as described in the U.S. Pat. No. 5,605,680; organosiloxanes containing benzmalonate groups as described in the European Patent Publications EP 0358584 B1, EP 0538431 B1 and EP 0709080 A1.

Antioxidants

Based on the invention all known antioxidants usually formulated into personal care and household products can be used. Especially preferred are antioxidants chosen from the group consisting of amino acids (e.g. glycine, histidine, tyrosine, tryptophan) and their derivatives, imidazole (e.g. urocanic acid) and derivatives, peptides such as D,L-carnosine, D-carnosine, L-carnosine and derivatives (e.g. anserine), carotenoids, carotenes (e.g. α-carotene, β-carotene, lycopene) and derivatives, chlorogenic acid and derivatives, lipoic acid and derivatives (e.g. dihydrolipoic acid), aurothioglucose, propylthiouracil and other thiols (e.g. thioredoxine, glutathione, cysteine, cystine, cystamine and its glycosyl-, N-acetyl-, methyl-, ethyl-, propyl-, amyl-, butyl- and lauryl-, palmitoyl-; oleyl-, γ-linoleyl-, cholesteryl- and glycerylester) and the salts thereof, dilaurylthiodipropionate, distearylthiodipropionate, thiodipropionic acid and its derivatives (ester, ether, peptides, lipids, nucleotides, nucleosides and salts) as well as sulfoximine compounds (such as buthioninsulfoximine, homocysteinesulfoximine, buthioninsulfone, penta-, hexa-, heptathioninsulfoximine) in very low compatible doses (e.g. pmol bis µmol/kg), additionally (metal)-chelators (such as α-hydroxyfatty acids, palmic-, phytinic acid, lactoferrin), β-hydroxyacids (such as citric acid, lactic acid, malic acid), huminic acid, gallic acid, gallic extracts, bilirubin, biliverdin, EDTA, EGTA and its derivatives, unsaturated fatty acids and their derivatives (such as γ-linoleic acid, linolic acid, oleic acid), folic acid and its derivatives, ubiquinone and ubiquinol and their derivatives, vitamin C and derivatives (such as ascorbylpalmitate and ascorbyltetraisopalmitate, Mg-ascorbylphosphate, Na-ascorbylphosphate, ascorbyl-acetate), tocopherol and derivates (such as vitamin-E-acetate), mixtures of nat. vitamin E, vitamin A and derivatives (vitamin-A-palmitate and -acetate) as well as coniferylbenzoate, rutinic acid and derivatives, α-glycosylrutin, ferulic acid, furfurylideneglucitol, carnosine, butylhydroxytoluene, butylhydroxyanisole, trihydroxybutyrophenone, urea and its derivatives, mannose and derivatives, zinc and derivatives (e.g. $ZnO$, $ZnSO_4$), selen and derivatives (e.g. selenomethionin), stilbenes and derivatives (such as stilbenoxide, trans-stilbenoxide) and suitable derivatives (salts, esters, ethers, sugars, nucleotides, nucleosides, peptides and lipids) of the named active ingredients. One or more preservatives/antioxidants may be present in an amount of at least 0.01 wt. % of the total weight of the composition. Preferably about 0.01 wt. % to about 10 wt. % of the total weight of the composition of the present invention is present. Most preferred, one or more preservatives/antioxidants are present in an amount about 0.1 wt. % to about 1 wt. %.

Surface Active Ingredients

Typically personal care products or household products also contain surface active ingredients like emulsifiers, solubilizers and the like. An emulsifier enables two or more immiscible components to be combined homogeneously. Moreover, the emulsifier acts to stabilize the composition. Emulsifiers that may be used in the present invention in order to form O/W, W/O, O/W/O or W/O/W emulsions/microemulsions include sorbitan oleate, sorbitan sesquioleate, sorbitan isostearate, sorbitan trioleate, polyglyceryl-3-diisostearate, polyglycerol esters of oleic/isostearic acid, polyglyceryl-6 hexaricinolate, polyglyceryl-4-oleate, polygylceryl-4 oleate/PEG-8 propylene glycol cocoate, oleamide DEA, TEA myristate, TEA stearate, magnesium stearate, sodium stearate, potassium laurate, potassium ricinoleate, sodium cocoate, sodium tallowate, potassium castorate, sodium oleate, and mixtures thereof. Further exemplary emulsifiers are phosphate esters and the salts thereof such as cetyl phosphate (Amphisol® A), diethanolamine cetyl phosphate (Amphisol®), potassium cetyl phosphate (Amphisol® K), sodium glyceryl oleate phosphate, hydrogenated vegetable glycerides phosphate and mixtures thereof. Furthermore, one or more synthetic polymers may be used as an emulsifier. For example, PVP eicosene copolymer, acrylates/$C_{10-30}$ alkyl acrylate crosspolymer, acrylates/steareth-20 methacrylate copolymer, PEG-22/dodecyl glycol copolymer, PEG-45/dodecyl glycol copolymer, and mixtures thereof. Further exemplary emulsifiers are fatty alcohols, e.g. cetearyl alcohol (Lanette O, Cognis Cooperation), cetyl alcohol (Lanette 16, Cognis Cooperation), stearyl alcohol (Lanette 18, Cognis Cooperation), Laneth-5 (Polychol 5, Croda Chemicals), furthermore sucrose and glucose derivatives, e.g. sucrose distearate (Crodesta F-10, Croda Chemicals), Methyl glucose isostearate (Isolan IS, Degussa Care Chemicals), furthermore ethoxylated carboxylic acids or polyethyleneglycol esters and polyethyleneglycol ethers, e.g. steareth-2 (Brij 72, Uniqema), steareth-21 (Brij 721, Uniqema), ceteareth-25 (Cremophor A25, BASF Cooperation), PEG-40 hydrogenated castor oil (Cremophor RH-40, BASF Cooperation), PEG-7 hydrogenated castor oil (Cremophor WO7, BASF Cooperation), PEG-30 Dipolyhydroxystearate (Arlacel P 135, Uniqema), furthermore glyceryl esters and polyglyceryl esters, e.g. polyglyceryl-3-diisostearate (Hostacerin TGI, Clariant Cooperation), polyglyceryl-2 dipolyhydroxystearate (Dehymuls PGPH, Cognis Cooperation), polyglyceryl-3 methylglucose distearate (Tego Care 450, Degussa Care Chemicals). The preferred emulsifiers are cetyl phosphate (Amphisol® A), diethanolamine cetyl phosphate (Amphisol®), potassium cetyl phosphate (Amphisol® K), PVP Eicosene copolymer, acrylates/$C_{10-30}$-alkyl acrylate crosspolymer, PEG-20 sorbitan isostearate, sorbitan isostearate, and mixtures thereof. The one or more emulsifiers are present in a total amount of at least 0.01 wt. % of the total weight of the composition. Preferably about 0.01 wt. % to about 20 wt. % of the total weight of the composition of the present invention is used. Most preferred, about 0.1 wt. % to about 10 wt. % of emulsifiers are used. Typically personal care products or household products also contain anionic, neutral, amphoteric or cationic tensides.

Exemplary anionic tensides comprise alkylsulfate, alkylethersulfate, alkylsulfonate, alkylarylsulfonate, alkylsuccinate, alkylsulfosuccinate, N-alkoylsarkosinate, acyltaurate, acylisethionate, alkylphosphate, alkyletherphosphate, alkylethercarboxylate, alpha-olefinesulfonate, especially the alkali-und earth alkali salts, e.g. sodium, potassium, magnesium, calcium, as well as ammonium- and triethanol aminesalts. The alkylethersulfate, alkyletherphosphate and alkylethercarboxylate may comprise between 1 to 10 ethyleneoxide or propyleneoxide units, preferably 1 to 3 ethyleneoxide-units per molecule.

Suitable are e.g. sodium laurylsulfate, ammonium lauryl sulfate, sodium laurylethersulfate, ammonium laurylethersulfate, sodium lauroylsarkonisate, sodiumoleylsuccinate, ammonium laurylsulfosuccinate, sodium dodecylbenzolsulfonate, triethanolamidodecylbenzolsulfonate.

Suitable amphoteric tensides are e.g. alkylbetaine, alkylamidopropylbetaine, alkylsulfobetaine, alkylglycinate, alkylcarboxyglycinate, alkylamphoacetate or propionate, alkylamphodiacetate or dipropionate such as cocodimethylsulfopropylbetaine, laurylbetaine, cocamidopropylbetaine or sodium cocamphopropionate.

Examples of non ionic tensides are e.g. reaction products of aliphatic alcohols or alkylphenols with 6 to 20 C-Atoms of a linear or branched alkyl chain with ethyleneoxide and/or propyleneoxide. The amount of alkyleneoxide is about 6 to mole to one mol alcohol. Furthermore alkylaminoxide, mono- or dialkylalkanolamide, fatty esters of polyethylene glycols, alkylpolyglycosides or sorbitanether ester are suitable for the incorporation of hair care compositions according to the invention.

Furthermore, the personal care products or household products may contain the usual cationic tensides such as quaternised ammonium compounds e.g. cetyltrimethylammoniumchloride or bromide (INCI: cetrimoniumchloride or bromide), hydroxyethylcetyldimonium phosphate (INCI: Quaternium-44), Luviquat®Mono LS (INCI: Cocotrimoniummethosulfate), poly(oxy-1,2-Ethandiyl), (OctadecylInitrilio) tri-2, 1-Ethandiyl) tris-(hydroxy)-phosphate (INCI Quaternium-52). For special effects typical conditioning agents may be combined with the condensation polymers within personal care products or household products, especially within hair care preparations such as the previously mentioned cationic polymers named polyquaternium (INCI), especially copolymers of vinylpyrrolidone/N-vinylimidazoliumsalts (Luviquat® FC, Luviquat® HM, Luviquat® MS, Luviquat® Ultracare), copolymers of N-vinylpyrrolidone/dimethylaminoethylmethacrylate quaternised with diethylsulfate (Luviquat® PQ 11), copolymers of N-cationic cellulose derivatives (Polyquaternium-4 and -10), acrylamidcopolymers (Polyquaternium-7). Furthermore protein hydrolysates may be used as well as conditioning agents on silicone basis such as polyarylsiloxane, polyarylalkylsiloxane, polyethersiloxane or silicone resins. Other suitable silicone compounds are dimethicondopolyole (CTFA) and amino functionalised silicone derivatives such as amodimethicone (CTFA).

Furthermore cationic guar derivatives such as guarhydroxypropyltrimoniumchloride (INCI) may be used.

The one or more anionic, neutral, amphoteric or cationic tensides are present in a total amount of at least 0.01 wt. % of the total weight of the composition. Preferably about 0.01 wt. % to about 20 wt. % of the total weight of the composition of the present invention is used. Most preferred, about 0.1 wt. % to about 10 wt. % of one or more tensides are used.

Oil and Fatty Components

The lipid phase can advantageously be chosen from mineral oils and mineral waxes; oils such as triglycerides of caprinic acid and/or caprylic acid or castor oil; oils or waxes and other natural or synthetic oils, in an preferred embodiment esters of fatty acids with alcohols e.g. isopropanol, propyleneglycol, glycerin or esters of fatty alcohols with carbonic acids or fatty acids; alkylbenzoates; and/or silicone oils.

Exemplary fatty substances which can be incorporated in the oil phase of the emulsion, microemulsion, oleo gel, hydrodispersion or lipodispersion of the present invention are advantageously chosen from esters of saturated and/or unsaturated, linear or branched alkyl carboxylic acids with 3 to 30 carbon atoms, and saturated and/or unsaturated, linear and/or branched alcohols with 3 to 30 carbon atoms as well as esters of aromatic carboxylic acids and of saturated and/or unsaturated, linear or branched alcohols of 3-30 carbon atoms. Such esters can advantageously be selected from octylpalmitate, octylcocoate, octylisostearate, octyldodecylmyristate, cetearylisononanoate, isopropylmyristate, isopropylpalmitate, isopropylstearate, isopropyloleate, n-butylstearate, n-hexyllaurate, n-decyloleate, isooctylstearate, isononylstearate, isononylisononanoate, 2-ethyl hexylpalmitate, 2-ethylhexyllaurate, 2-hexyldecylstearate, 2-octyldodecylpalmitate, stearylheptanoate, oleyloleate, oleylerucate, erucyloleate, erucylerucate, tridecylstearate, tridecyltrimellitate, as well as synthetic, half-synthetic or natural mixtures of such esters e.g. jojoba oil. Other fatty components suitable for personal care products or household products of the present invention include polar oils such as lecithins and fatty acid triglycerides, namely triglycerol esters of saturated and/or unsaturated, straight or branched carboxylic acid with 8 to 24 carbon atoms, preferably of 12 to 18 carbon atoms whereas the fatty acid triglycerides are preferably chosen from synthetic, half synthetic or natural oils (e.g. cocoglyceride, olive oil, sun flower oil, soybean oil, peanut oil, rape seed oil, sweet almond oil, palm oil, coconut oil, castor oil, hydrogenated castor oil, wheat oil, grape seed oil, macadamia nut oil and others); apolar oils such as linear and/or branched hydrocarbons and waxes e.g. mineral oils, vaseline (petrolatum); paraffins, squalane and squalene, polyolefines, hydrogenated polyisobutenes and isohexadecanes, favored polyolefines are polydecenes; dialkyl ethers such as dicaprylylether; linear or cyclic silicone oils such as preferably cyclomethicone (octamethylcyclotetrasiloxane; cetyldimethicone, hexamethylcyclotrisiloxane, polydimethylsiloxane, poly(methylphenylsiloxane) and mixtures thereof.

Other fatty components which can advantageously be incorporated in personal care products or household products of the present invention are isoeikosane; neopentylglycoldiheptanoate; propyleneglycoldicaprylate/dicaprate; caprylic/capric/dig lycerylsuccinate; butyleneglycol caprylat/caprat; $C_{12-13}$-alkyllactate; di-$C_{12-13}$-alkyltartrate; triisostearin; dipentaerythrityl hexacaprylat/hexacaprate; propyleneglycolmonoisostearate; tricaprylin; dimethylisosorbid. Especially beneficial is the use of mixtures $C_{12-15}$-alkylbenzoate and 2-ethylhexylisostearate, mixtures $C_{12-15}$-alkylbenzoate and isotridecylisononanoate as well as mixtures of $C_{12-15}$-alkylbenzoate, 2-ethylhexylisostearate and isotridecylisononanoate.

The oily phase of the formulation of the present invention can also contain natural vegetable or animal waxes such as bee wax, china wax, bumblebee wax and other waxes of insects as well as shea butter and cocoa butter.

Silicone Oils

Suitable silicone oils are e.g. such as dimethylpolysiloxane, diethylpolysiloxane, diphenylpolysiloxane, cyclic siloxanes, poly(methylphenylsiloxanes) as well as amino-, fatty acid-, alcohol-, polyether-, epoxy-, fluoro-, glycoside-, and/or alkyl modified silicone compounds which are liquid or solid at room temperature and mixtures thereof. The number average molecular weight of the dimethicones and poly(methylphenylsiloxanes) is preferably in the range of 100 to 150000 g/mol. Preferred cyclic siloxanes comprise 4- to 8-membered rings which are for example commercially available as cyclomethicones.

An oil or fatty component is present in an amount of about 1 wt. % to about 50 wt. % of the total weight of the product. The preferred amount of an oil or fatty component is about 2 wt. % to about 25 wt. %, and most preferably about 3 wt. % to about 20 wt. %.

Moisturizing Agents

A moisturizing agent may be incorporated into a product of the present invention to maintain hydration or rehydrate the skin. Moisturizers that prevent water from evaporating from the skin by providing a protective coating are called emollients. Additionally an emollient provides a softening or soothing effect on the skin surface and is generally considered safe for topical use. Preferred emollients include mineral oils, lanolin, petrolatum, capric/caprylic triglyceraldehydes, cholesterol, silicones such as dimethicone, cyclomethicone, almond oil, jojoba oil, avocado oil, castor oil, sesame oil, sunflower oil, coconut oil and grape seed oil, cocoa butter, olive oil, aloe extracts, fatty acids such as oleic and stearic, fatty alcohols such as cetyl and hexadecyl (ENJAY), diisopropyl adipate, hydroxybenzoate esters, benzoic acid esters of $C_{9-15}$-alcohols, isononyl iso-nonanoate, ethers such as polyoxypropylene butyl ethers and polyoxypropylene cetyl ethers, and $C_{12-15}$-alkyl benzoates, and mixtures thereof. The most preferred emollients are hydroxybenzoate esters, aloe vera, $C_{12-15}$-alkyl benzoates, and mixtures thereof. An emollient is present in an amount of about 1 wt. % to about 50 wt. % of the total weight of the product. The preferred amount of emollient is about 2 wt. % to about 25 wt. %, and most preferably about 3 wt. % to about 15 wt. %.

Moisturizers that bind water, thereby retaining it on the skin surface are called humectants. Examples of humectants which can be incorporated into a product of the present invention are glycerin, propylene glycol, polypropylene glycol, polyethylene glycol, lactic acid, sodium lactate, pyrrolidone carboxylic acid, urea, phospholipids, collagen, elastin, ceramides, lecithin, sorbitol, PEG-4, and mixtures thereof. Additional suitable moisturizers are polymeric moisturizers of the family of water soluble and/or swellable/and/or with water gelating polysaccharides such as hyaluronic acid, chitosan and/or a fructose rich polysaccharide which is e.g. available as Fucogel®1000 (CAS-Nr. 178463-23-5) by SOLABIA S. One or more humectants are optionally present at about 0.5 wt. % to about 8 wt. % in a product of the present invention, preferably about 1 wt. % to about 5 wt. %.

The aqueous phase of the products of the present invention can contain the usual cosmetic additives such as alcohols, especially lower alcohols, preferably ethanol and/or isopropanol, low diols or polyols and their ethers, preferably propyleneglycol, glycerin, ethyleneglycol, ethyleneglycol monoethyl- or monobutylether, propyleneglycol monomethyl- or -monoethyl- or -monobutylether, diethyleneglycol monomethyl- or monoethylether and analogue products, polymers, foam stabilizers; electrolytes and especially one or more thickeners.

Thickeners

Thickeners that may be used in formulations of the present invention to assist in making the consistency of a product suitable include carbomer, siliciumdioxide, magnesium and/or aluminum silicates, lipid thickeners, e.g. cetyl alcohol, cetyl palmitate (Cutina CP, Cognis Cooperation), glyceryl myristate (Estol 3650, Uniqema), microcrystalline wax (A&E Connock), myristyl alcohol (Lanette 14, Cognis Cooperation), myristyl lactate (Crodamol ML, Croda Chemicals), beeswax (A&E Connock), stearic acid (Lipo Chemicals), stearyl alcohol (Lanette 18, Cognis Cooperation), polysaccharides and their derivatives such as xanthan gum (Keltrol, CP Kelco), hydroxypropyl cellulose (Klucel, Hercules Incorporated), Hydroxyethylcellulose (Tylose H, Clariant Corporation), polyacrylamides, selfemulsifying polyacrylamide, e.g. Salcare SC 91, Salcare SC 96 (Ciba Specialty Chemicals), Sepigel 305 (Seppic), acrylate crosspolymers, preferably a carbomer, such as Carbopole® of type 980, 981, 1382, 2984, 5984, ETD 2001, ETD 2050, Ultrez 10, Ultrez 21 (Noveon Inc.), alone or mixtures thereof. Thickeners can be present in an amount of about 6.01 wt. % to about 8 wt. % in the product of the present invention, preferably, 0.05 wt. % to about 5 wt. %.

Neutralizing Agents

Examples of neutralizing agents which may be included in the product of the present invention to neutralize components such as e.g. an emulsifier or a foam builder/stabilizer include but are not limited to alkali hydroxides such as a sodium and potassium hydroxide; organic bases such as diethanolamine (DEA), triethanolamine (TEA), aminomethyl propanol, and mixtures thereof; amino acids such as arginine and lysine and any combination of any foregoing. The neutralizing agent can be present in an amount of about 0.01 wt. % to about 8 wt. % in the product of the present invention, preferably, 1 wt. % to about 5 wt. %.

Electrolytes

The addition of electrolytes into the product of the present invention may be necessary to change the behavior of a hydrophobic emulsifier. Thus, the emulsions/microemulsions of this invention may contain preferably electrolytes of one or several salts including anions such as chloride, sulfate, carbonate, borate and aluminate, without being limited thereto. Other suitable electrolytes can be on the basis of organic anions such as, but not limited to, lactate, acetate, benzoate, propionate, tartrate and citrate. As cations preferably ammonium, alkylammonium, alkali- or alkaline earth metals, magnesium-, iron- or zinc-ions are selected. Especially preferred salts are potassium and sodium chloride, magnesium sulfate, zinc sulfate and mixtures thereof. Electrolytes can be present in an amount of about 0.01 wt. % to about 8 wt. % in the product of the present invention.

Light Stabilizers

The addition of further light stabilizers may be desirable. Such light stabilizers are e.g. known as sterically hindered amine light stabilizer (HALS) which can be of monomeric or polymeric nature. They are for example selected from the group consisting of N,N'-bisformyl-N,N'-bis-(2,2,6,6-tetramethyl-4-piperidinyl)-hexamethylenediamine (Uvinul 4050 H), bis-(2,2,6,6-tetramethyl-4-piperidyl)sebacate (Uvinul 4077 H), bis-(1,2,2,6,6-pentamethyl-4-piperidyl)-sebacate+methyl-(1,2,2,6,6-pentamethyl-4-piperidyl)sebacate. (Uvinul 4092 H), bis-(2,2,6,6-tetramethylpiperidine-4-yl)-sebacate, bis-(2,2,6,6-tetramethylpiperidine-4-yl) succinate, bis-(1,2,2,6,6-pentamethylpiperidine-4-yl) sebacate, n-butyl-3,5-di-tert-butyl-4-hydroxybenzyl-malonic acid bis-(1,2,2,6,6-pentamethylpiperidyl) ester, the condensate of 1-hydroxyethyl-2,2,6,6-tetramethyl-4-hydroxypiperidine and succinic acid, the condensate of N,N'-bis-(2,2,6,6-tetramethyl-4-piperidyl)hexamethylenediamine and 4-tert-octylamino-2,6-dichloro-1,3,5-s-triazine, tris-(2,2,6,6-tetramethyl-4-piperidyl)nitrilotriacetate, tetrakis-(2,2,6,6-tetra-methyl-4-piperidyl)-1,2,3,4-butanetetranoate, 1,1'-(1, 2-ethanediyl)-bis (3,3,5,5-tetramethylpiperazinone), 4-benzoyl-2,2,6,6-tetramethylpiperidine, 4-stearyloxy-2,2,6, 6-tetramethylpiperidine, bis-(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dione, the condensate of N,N-bis-(2,2,6,6-tetramethyl-4-piperidyl) hexamethylenediamine and 4-morpholino-2,6-dichloro-1,3,5-triazine, the condensate of 2-chloro-4,6-di(4-n-butylamino-2,2,6,6-tetramethylpiperidyl)-1,3,5-triazine and 1,2-bis-(3-aminopropylamino) ethane, the condensate of 2-chloro-4,6-di(4-n-butylamino-1, 2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]-decane-2,4-dione, 3-dodecyl-1-(2,2,6,6-tetramethyl-4-piperidyl)pyrrolidin-2, 5-dione, 3-dodecyl-1-(1,2,2,6,6-pentamethyl-4-piperidyl)-pyrrolidine-2,5-dione, a mixture of 4-hexadecyloxy- and 4-stearyloxy-2,2,6,6-tetramethylpiperidine, the condensate of N,N'-bis-(2,2,6,6-tetramethyl-4-piperidyl)hexamethyl-enediamine and 4-cyclohexylamino-2,6-dichloro-1,3,5-triazine, the condensate of 1,2-bis(3-aminopropylamino) ethane and 2,4,6-trichloro-1,3,5-triazine and 4-butylamino-2,2,6,6-tetramethylpiperidine (CAS reg. No. [136504-96-6]); (2,2,6,6-tetramethyl-4-piperidyl)-n-dodecylsuccinimide, (1,2,2,6,6-pentamethyl-4-piperidyl)-n-dodecylsuccinimide, 2-undecyl-7,7,9,9-tetramethyl-1-oxa-3,8-diaza-4-oxo-spiro [4,5]decane, the reaction product of 7,7,9,9-tetramethyl-2-cycloundecyl-1-oxa-3,8-diaza-4-oxospiro[4,5]decane and epichlorohydrin without being limited thereto.

Insect Repellents

Examples of insect repellents which can be used in products according to the invention are for example N,N-diethyl-m-toluamide, 1,2-pentanediol or insect repellant 3535.

Self Tanning Ingredients

Examples of self tanning ingredients are e.g. dihydroxyacetone and/or erythrulose or dihydroxy acetone and/or dihydroxyacetone precursors as described in WO 01/85124 and/or erythrulose.

Skin Whitening Ingredients

Examples of skin whitening ingredients are for example vitamin C, sodium ascorbyl phosphate and magnesium ascorbyl phosphate, arbutin and alpha-arbutin.

Deodorizing Active Ingredients

Examples of deodorizing active ingredients which come into consideration are antiperspirants such as aluminum chlorohydrates, aluminum hydroxyacetates and acidic aluminum/zirconium salts. Esterase inhibitors may be added as further deodorizing active ingredients. Such inhibitors are preferably trialkyl citrates, such as trimethyl citrate, tripropyl citrate, triisopropyl citrate, tributyl citrate and especially triethyl citrate (Hydagen CAT, Henkel), which inhibit enzyme activity and hence reduce odor formation. Further substances that come into consideration as esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid or tartaric acid diethyl ester. Antibacterial active ingredients that influence the germ flora and kill or inhibit the growth of sweat-decomposing bacteria can likewise be present in the preparations (especially in stick preparations). Other antibacterials which could be present are chitosan, phenoxyethanol and chlorhexidinegluconate-5-chloro-2-(2,4-dichlorophenoxy)-phenol (Triclosan, Irgasan, Ciba Specialty Chemicals Inc.).

Anti-Dandruff Agents

Examples of anti-dandruff agents which may be used are climbazole, octopirox and zinc pyrithione.

Film Formers

Customary film formers include, for example, chitosan, microcrystalline chitosan, quaternized chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds.

Preservatives

Examples of preservatives include Methyl-, Ethyl-, Propyl-, Butylparabens, Benzalkonium chloride, 2-Bromo-2-nitro-propane-1,3-diol, Dehydroacetic acid, Diazolidinyl Urea, 2-Dichlorobenzyl alcohol, DMDM hydantoin, Formaldehyde solution, Methyldibromoglutaronitrile, Phenoxyethanol, Sodium Hydroxymethylglycinate, Imidazolidinyl Urea, Triclosan and further substance classes listed in the following reference: K. F. De Polo-A short textbook of cosmetology, Chapter 7, Table 7-2, 7-3, 7-4 and 7-5, p 210-219.

Bacteria-Inhibiting Agents

Typical examples of bacteria-inhibiting agents are preservatives that have a specific action against gram-positive bacteria, such as 2,4,4'-trichloro-2'-hydroxydiphenyl ether, chlorhexidine (1,6-di-(4-chlorophenyl-biguanido) hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorizing agent of interest is the terpene alcohol farnesol (3,7,11-trimethyl-2,6,10-dodecatrien-1-ol), which is present in lime blossom oil. Glycerolmonolaurate has also proved to be a bacteriostatic agent. The amount of the additional bacteria-inhibiting agents present is usually from 0.1 to 2 wt. %, based on the solids content of the preparations.

Polymers

The products according to the invention may comprise additional cosmetically and dermatologically acceptable polymers which is different from the condensation polymer in order to established the desired properties. For this purpose all anionic, cationic, amphoteric or neutral polymers may be used.

Examples for anionic polymers are homo- and copolymers of acrylic acid or methacrylic acid and the salts thereof; copolymers of acrylic acid and acrylamide and the salts thereof; sodium salts of polyhydroxy carbonic acids, water soluble or water dispersable polyester; polyurethanes such as Luviset Pur® of BASF and polyureas. Especially suitable are copolymers of t-butyl acrylate, ethylacrylate, methyl acrylic acid (e.g. Luvimer® 100P); copolymers of ethylacrylate and methacrylic acid (e.g. Luviflex® Soft); copolymers of N-tert.-butyl-acrylamide, ethylacrylate and acrylic acid (Ultrahold®, strong); copolymers of vinylacetate, crotonic acid and eventually other vinylic esters (e.g. Luviset® grades); copolymers of maleic acid anhydride; eventually with alcohols reacted anionic polysiloxanes e.g. carboxy functionalized, t-butylacrylate, methacrylic acid (Luviskol® VBM); copolymers of acrylic acid and methacrylic acid with hydrophobic monomers such as C4-C30 alkylester of methacrylic acid, C4-C30-alkylvinylester, C4-C30-alkylvinylether and hyaluronic acid. Examples of anionic polymers are also vinylacetate/crotonic acid copolymers (Resyn® by National Starch or Gafset® by GAF); vinylpyrrolidone/vinylacrylate copolymers (e.g. Luviflex® by BASF). Other suitable polymers are vinylpyrrolidone/acrylate terpolymer and sodiumsulfonate containing polyamides or sodiumsulfonate containing polyesters.

Additional polymers which can be used in combination with the condensation polymers comprises Balance® CR (National Starch; Acrylate Copolymer), Balance® 0/55 (National Starch; Acrylate Copolymer), Balances® 47 (National Starch; Octylacrylamid/Acrylate/Butylaminoethylmethacrylate-Copolymer), Aquaflex® FX 64 (ISP; Isobutylene/Ethylmaleimid/Hydroxyethylmaleimid-Copolymer), Aquaflex® SF-40 (ISP/National Starch; VPNinylcaprolactam/DMAPA Acrylate Copolymer), Allianz® LT-120 (ISP/Rohm & Haas; Acrylat/C1-2 succinate/hydroxyacrylate copolymer), Aquarez® HS (Eastman; Polyester-1), Diaformer® Z-400 (Clariant; Methacryloylethylbetaine/Methacrylate-Copolymer), Diaformer® Z-711 (Clariant; Methacryloylethyl N-oxide/Methacrylate-Copolymer), Diaformer® Z-712 (Clariant; Methacryloylethyl N-oxide/MethacrylateCopolymer), Omnirez® 2000 (ISP; Monoethylester from Poly (Methylvinylether/Maleic Acid in Ethanol), Amphomer® HC (National Starch; Acrylate/Octylacrylamide-Copolymer), Amphomer® 28-4910 (National Starch; Octyl-acrylamide/Acrylate/Butylaminoethylmethacrylate-Copolymer), Advantage® HC 37 (ISP; Terpolymer of vinylcaprolactam/N-vinylpyrrolidone/dimethylaminoethylmethacrylate), Advantage® LC55 and LC80 or LC A and LC E, Advantage®Plus (ISP; VA/butylmaleate/isobornylacrylate copolymer), Aculyne®258 (Rohm & Haas; Acrylate/Hydroxyesteracrylate-Copolymer), Luviset® P.U.R. (BASF, Polyurethane-1), Luviflex® Silk (BASF), Eastman® AQ 48 (Eastman), Styleze® CC-10 (ISP; VP/DMAPA Acrylates Copolymer), Styleze® 2000 (ISP; VP/Acrylates/Lauryl Methacrylate Copolymer), DynamX (National Starch; Polyurethane-14 AMP-Acrylates Copolymer), Resyn XP (National Starch; Acrylates/Octylacrylamide Copolymer), Fixomer A-30 (OndeoNalco; poly-methacrylic acid (and) acrylamidomethyl propanesulfonic acid), Fixate G-100 (Noveon; AMP-Acrylates/Allyl Methacrylate Copolymer).

Examples of cationic polymers are Polyquaternium (INCI), e.g. copolymers of vinylpyrrolidone/N-vinylimidazolium salts (Luviquat®FC, Luviquat® HM, Luviquat®MS, Luviquat®Ultracare), copolymers of N-vinylpyrrolidone/dimethylaminoethylmethacrylate, quaternized with diethylsulfate (Luviquat® PQ 11, INCI: Polyquaternium-11), copolymers of N-vinylcaprolactam/N-vinyl-pyrrolidone/N-vinylimidazolium salts (Luviquat®Hold; INCI: Polyquaternium-46); cationic derivatives of cellulose (Polyquaternium-4 and -10), acrylamidocopolymers (Polyquaternium-7), Chitosan, cationic starch derivatives (INCI: starch hydroxypropyltrimonium chloride, corn starch modified), cationic guar derivates (INCI: hydroxypropyl guar hydroxypropyltrimonium chloride), cationic sun flower seed derivatives (INCI: sun flower seed amidopropyl hydroxyethyldimonium chloride), copolymers of acrylic acid, acrylamide and methacrylamidopropyltrimoniumchloride (INCI: Polyquaternium-53), Polyquaternium-32, Polyquaternium-28 without being limited thereto. Suitable cationic quaternized polymers are furthermore Merquat® (polymers on the basis of dimethyldiallyl ammoniumchloride), Gafquat® (quaternary polymers formed by reacting polyvinylpyrrolidone with quaternary ammonium compounds); Polymer JR (hydroxyethylcellulose with cationic groups), and cationic polymers on plant basis such as guar polymers, commercially available as Jaguar® grades of Rhodia.

Examples of neutral polymers are polyvinylpyrrolidone, copolymers of N-vinylpyrrolidone and vinylacetate and/or vinylpropionate, polysiloxane, polyvinylcaprolactam and other copolymers of N-vinylpyrrolidone, copolymers of N-vinylpyrrolidone and alkylacrylate or methacrylate monomers with C1-C18 alkyl chains, copolymers of polyvinylalcohol and polyalkyleneglycole such as Kollicoats® IR (BASF) or copolymers of other vinyl monomers to polyalkyleneglycol, polysiloxane, polyvinylcaprolactam and copolymers with N-Vinylpyrrolidone, polyethyleneimine and the salts thereof, polyvinylamine and the salts thereof, cellulose derivatives, chitosan, polyasparaginic acid salts and derivatives thereof, polyethyleneimine and the salts thereof, polyvinylamine and the salts thereof such as Luviflex® Swing (partly hydrolysed copolymer of polyvinylacetate and polyethyleneglycol by BASF).

Suitable polymers are also non-ionic, water soluble respectively water dispersible polymers or oligomers such as polyvinylcaprolactam, e.g. Luviskol® Plus (BASF), or polyvinylpyrrolidone and copolymers with e.g. vinylesters such as vinylacetate e.g. Luviskol® VA 37 (BASF); polyamide e.g. on the basis of itaconic acid and aliphatic diamines as e.g. described in DE-A-43 33 23.

Examples of amphoteric or zwitterionic polymers are octylacrylamide/methyl methacrylate/tert-butylaminoethyl methacrylate/2-hydroxypropyl methacrylate copolymers e.g. obtainable under the names Amphomer® (Delft National) and zwitterionic polymers as disclosed, for example, in German Patent Applications DE 39 29 973, DE 21 50 557, DE 28 17 369 and DE 37 08 451. Preferred zwitterionic polymers are acrylamidopropyltrimethylammonium chloride/acrylic acid or methacrylic acid copolymers and their alkali metal and ammonium salts. Other suitable polymers are methacroylethylbetaine/methacrylate copolymers, which are obtainable commercially under the name Amersette® (AMERCHOL) and copolymers of hydroxyethyl methacrylate, methyl methacrylate, N,N-dimethylaminoethyl methacrylate and acrylic acid (Jordapon®);

Additional suitable polymers are nonionic, siloxane-containing, water-soluble or -dispersible polymers, e.g. polyether siloxanes, such as Tegopren(R) (Goldschmidt) or Belsil (R) (Wacker).

Scents and Fragrances

The personal care products and household products according to the invention may contain scents and fragrances comprising at least one, preferably numerous odorant ingredients of natural and/or synthetic origin. The range of the natural odorants includes, in addition to readily volatile, also moderately and only slightly volatile components. The synthetic odorants embrace representatives from practically all classes of odorant substances.

The following list comprises examples of known odorants which may be stabilized with the stabilizing composition according to the invention without being limited thereto:

natural products such as tree moss absolute, basil oil, tropical fruit oils (such as bergamot oil, mandarin oil, etc.), mastix absolute, myrtle oil, palmarosa oil, patchouli oil, petitgrain oil, wormwood oil, lavender oil, rose oil, jasmine oil, ylang-ylang oil, etc.;

alcohols: farnesol, geraniol, linalool, nerol, phenylethyl alcohol, rhodinol, cinnamic alcohol, (Z)-hex-3-en-1-ol, menthol, a-terpineol, etc.;

aldehydes such as citral, alpha-hexyl cinnamaldehyde, Lilial, methylionone, verbenone, nootkatone, geranylacetone, etc.;

esters such as allyl phenoxyacetate, benzyl salicylate, cinnamyl propionate, citronellyl acetate, decyl acetate, dimethylbenzylcarbinyl acetate, dimethylbenzylcarbinyl butyrate, ethyl acetoacetate, cis-3-hexenyl isobutyrate, cis-3-hexenyl salicylate, linalyl acetate, methyl dihydrojasmonate, styralyl propionate, vetiveryl acetate, benzyl acetate, geranyl acetate, etc.;

lactones such as gamma-undecalactone, delta-decalactone, pentadecanolide, 12-oxahexadecanolide, etc.;

acetals such as Viridine (phenylacetaldehyde dimethylacetal), etc.;

and other components often used in perfumery such as indole, p-mentha-8-thiol-3-one, methyleugenol, eugenol, anethol, etc.

Colorants

Generally, for the coloration of household products or personal care products according to the invention all substances are suitable which have an absorption in the visible light of electromagnetic radiation (400-4000 nm) The absorption is often caused by the following chromophores: Azo- (mono-, di-, tris-, or poly-)stilbene-, carotenoide-, diarylmethan-, triarylmethan-, xanthene-, acridine-, quinoline-, methin- (also polymethin-) thiazole-, indamine-, indophenol-, azine-, oxazine-, thiazine-, anthraquinone- indigo-, phthalocyanin and further synthetic, natural and/or inorganic chromophores.

FD&C and D&C which can be used in household products or personal care products according to the invention are e.g. curcumin, riboflavin, lactoflavin, tartrazine, chinolinyellow, cochenille, azorubin, amaranth, ponceau 4R, erythrosine, red 2G, indigotin, chlorophyll, chlorophyllin, caramel, carbo medicinalis, carotenoids, carotin, bixin, norbixin, annatto, orlean, capsanthin, capsorubin, lycopin, xanthophyll, flavoxanthin, lutein, kryptoaxanthin, rubixanthin, violaxanthin, rhodoxanthin, canthaxanthin, betanin, anthocyans without being limited thereto. Examples of dyes are e.g. inorganic pigments such as iron oxide (iron oxide red, iron oxide yellow, iron oxide black etc.) ultramarines, chromium oxide green or carbon black. Other colorants and dyes which can be stabilized with the stabilizing composition according to the invention comprise natural or synthetic organic pigments, disperse dyes which may be solubilized in solvents like direct hair dyes of the HC type, for example HC red No. 3, HC Blue No. 2 and all other hair dyes listed in International Cosmetic Ingredient Dictionary Handbook 7$^{th}$ edition 1997) or the dispersion dyes listed in Color Index International Society of Dyers and Colorist, color varnishes (insoluble salts of soluble dyes, like many Ca-, Ba- or Al-salts of anionic dyes), soluble anionic or cationic dyes such as acid dyes (anionic), basic dyes (cationic), direct dyes, reactive dyes or solvent dyes, fluorescent dyes, fluorescein and isothiocyanates.

Active Ingredients

Active ingredients which might be used in personal care products and household products according to the invention comprise vitamins such as tocopherol, ascorbic acid, ascorbyl phosphate, vitamin Q, D, and K, retinol, retinal, retinoic acid, retinol acetate, retinol palmitate, biotin, carotinoid derivatives such as beta carotene, lycopene, asthaxanthene, vegetable extracts, antibacterial ingredients, instable amino acids comprising dipeptides, oligopeptides and polypeptides such as methionen, cystein, cystin, tryptophan, phenylalanine, tyrosine, phenols, polyphenols or flavonoids, bisabolol, allantoin, phytantriol, panthenol, AHA acids, Ubichinones such as Coenzym Q 10, ceramides, pseudoceramides, essential oils, plant extracts deoxyribonucleic acid, protein hydrolysates.

Preferred body-care products are skin care preparations, preparations containing scents and/or fragrances, hair-care preparations, dentrifices, deodorant and antiperspirant, decorative preparations, light protection preparations and functional preparations.

Examples of skin care preparations are, in particular, body oils, body lotions, body creams, body gels, facial lotions, facial creams, facial gels, e.g. eye creams, anti-wrinkle creams, day care lotions, night creams, treatment creams, skin protection ointments, sunscreens, shaving preparations, such as shaving foams or gels, skin powders such as baby powder, moisturizing gels, moisturizing creams, moisturizing sprays, revitalizing body sprays, cellulite gels, anti acne preparations, cleansing milks and peeling preparations.

According to the invention the skin care preparations have a pH of 3-10, preferably pH 4-8.

Preparations containing scents and/or fragrances are in particular perfumes, toilet waters and shaving lotions (aftershave preparations).

Examples of hair care products are, for example, shampoo for humans and animals, hair conditioners, products for styling and treating hair, perming agents, hair sprays and lacquers, hair gels, hair fixatives and hair dying or bleaching agents.

Examples of dentifrices are in particular tooth cream, toothpastes, mouth-washes, mouth rinses, anti-plaque preparations and cleansing agents for dentures.

Examples of decorative preparations are in particular lipstick, nail varnishes, eye shadow, mascaras, dry and moist make-up, rouge, powders, depilatory agents, and suntan lotions.

Examples of functional preparations are cosmetic or dermatological compositions containing active ingredients such as hormone preparations, vitamin preparations, vegetable extract preparations and antibacterial preparations.

Personal care products in accordance with the invention such as cosmetic and dermatological compositions can be in the form of a liquid, lotion, a thickened lotion, a gel, a cream, a milk, an ointment, a paste, a powder, a make-up, or a solid tube stick and can be optionally be packaged as an aerosol and can be provided in the form of a mousse, foam or a spray foams, sprays, sticks or aerosols or wipes. The personal care products according to the invention can be packed as an ampoule. The personal care products according to the invention can be in the form of a suspension or dispersion in solvents or fatty substances, or alternatively in the form of an emulsion or micro emulsion (in particular of O/W or W/O type, O/W/O or W/O/W-type), such as a cream or a milk, a vesicular dispersion, in the form of an ointment, a gel, a solid tube stick or an aerosol mousse. The emulsions can also contain anionic, nonionic, cationic or amphoteric surfactants.

The condensation polymer may be present in the oil or in the aqueous or aqueous ethanolic phase.

The condensation polymers as defined above are especially suitable for personal care products, in particular:

skin-care preparations, e.g. skin-washing and cleansing preparations in the form of tablet-form or liquid soaps, sapless detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils;

body oils, body lotions, body gels; skin protection ointments; facial creams/lotions/gels; day care skin or facial creams/lotions/gels; night creams, eye creams/lotions/gels/ampoules; anti-wrinkle creams/lotions/gels/ampoules;

cosmetic personal care preparations, e.g. facial make-up in the form of day creams or powder creams, face powder (loose or pressed), rouge or cream make-up, eye-care preparations, e.g. eye shadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and antiperspirants or callus-removing preparations;

light-protective preparations, such as sun milks, lotions, creams or oils, facial day care products, unblocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons, pump-action sprays;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, pre-shave preparations for dry shaving, aftershaves or aftershave lotions;

scent or fragrance preparations, e.g. scent, fragrance and/or odorant ingredient containing preparations such as perfumes, eau de Colognes, eau de toilettes, eau de perfumes, eau de toilettes, perfume oils or perfume creams;

dentifrices, in particular tooth creams, toothpastes, mouth-washes, mouth rinses, anti-plaque preparations and cleansing agents for dentures;

decorative preparations, in particular lipsticks, nail varnishes, eye shadows, mascaras, dry and moist make-up, rouge, powders, depilatory agents and suntan lotions cosmetic formulations containing active ingredients, in particular hormone preparations, vitamin preparations, vegetable extract preparations and antibacterial preparations.

The final formulations listed may exist in a wide variety of presentation forms, for example in the form of liquid preparations, as a W/O, O/W, O/W/O, W/O/W or PIT emulsion and all kinds of micro emulsions, in the form of a gel, in the form of an oil, a cream, milk or lotion, in the form of a stick, in the form of a spray (spray with propellant gas or pump-action spray) or an aerosol, in the form of a foam, or in the form of a paste.

Especially preferred embodiments of the invention are hair care preparations containing the condensation polymer.

Hair-care preparations according to the invention contain the condensation polymer in a concentration of 0.1 to 30 wt. %, preferably 0.5 to 20 wt. % based on the total weight of the composition.

Preferably the hair care preparations are in the form of a cosmetic hair-treatment preparations, e.g. hair-washing preparations in the form of shampoos and conditioners, hair-care preparations, e.g. pre-treatment preparations, hair tonics, styling creams, styling gels, pomades, hair rinses, treatment packs, intensive hair treatments, e.g. leave-on and rinse-off deep conditioners, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidizing dyes, or natural hair colorants, such as henna or chamomile.

Based on the application the hair care preparations may be in the form of a (aerosol) spray, (aerosol) foam, gel, gel spray, cream, lotion or a wax. Hair sprays comprise as well aerosol sprays as pump sprays without propellant. Hair foams comprise as well aerosol foams as pump foams without propellant. Hair sprays and hair foams comprise mainly or exclusively water soluble or water dispersible components. If the components used in hair sprays or hair foams according to the invention are water dispersible, then they may be in the form of microdispersions with particle sizes of usually 1 to 350 nm, preferably 1 to 250 nm. The solid content of such preparations is typically in the range of 0.5 to 20 wt. % of the total weight of the preparation. Such microdispersions normally do not need further emulsifiers or tensides for their stabilization.

A preferred hair-treatment composition comprises:
1. 0.2 to 20 wt. % of a condensation polymer
2. 30 to 99.5 wt. %, preferably 40 to 99 wt. %, of at least one solvent chosen from water, water-miscible solvents and mixtures thereof
3. 0 to 70 wt. % of propellant
4. 0 to 10 wt. % of at least one water-soluble or water-dispersible hair polymer which is different from 1.)
5. 0 to 0.3% by weight of at least one water-insoluble silicone
6. 0 to 0.5 wt. % of at least one wax, preferably at least one fatty acid amide,
7. and customary additives.

The hair care preparations according to the invention can comprise, as component 4), at least one other water-soluble or water-dispersible hair polymer. The content of this component is then generally from about 0.1 to 10% by weight, based on the total weight of the composition. Here, it is preferable to use water-soluble or water-dispersible polyurethanes which, if desired, additionally comprise siloxane groups in copolymerized form.

The composition according to the invention can comprise, as component 5), at least one water-insoluble silicone, in particular a polydimethylsiloxane, e.g. the Abil® grades from Goldschmidt. The content of this component is then generally from about 0.0001 to 0.2% by weight, preferably from 0.001 to 0.1% by weight, based on the total weight of the composition. Preference is given to using at least one fatty acid amide, such as, for example, erucamide, as component 6).

The hair care preparations according to the invention can, where appropriate, additionally comprise an antifoam, e.g. one based on silicone. The amount of antifoam is generally up to 0.001% by weight, based on the total amount of the composition. The compositions according to the invention have the advantage that, on the one hand, they impart the desired hold to the hair and, on the other hand, the polymers are easy to wash out. Generally, a natural appearance and shine is imparted to the hair, even when the hair is by its very nature especially thick and/or dark.

In particular, the hair care preparations according to the invention can be formulated to give hair-treatment compositions, in particular hairsprays, with a high propellant content. Advantageously, the hair-treatment compositions according to the invention essentially do not have a "flaking" effect.

In a preferred embodiment, the hair care preparations according to the invention comprise:
1. 0.05 to 20 wt. % of at least one condensation polymer
2. 20 to 99.95 wt. % of water and/or alcohol
3. 0 to 79.5 wt. % of customary additives The term alcohols refers to all alcohols usually used in cosmetics such as ethanol, n-propanol, isopropanol without being limited thereto.

Customary additives are e.g. propellants, anti-foaming agents, surface active ingredients e.g. tensides, emulsifiers, foam former and solubilisators. The used surface active ingredients may be anionic, cationic, amphoteric or neutral. Further ingredients may be preservatives, antioxidants, perfume oils, lipidic refatters, active and/or caring ingredients such as panthenol, collagen, vitamins, protein hydrolysates, alpha- and beta hydroxylcarbonic acids, stabilisators, pH regulators, opacifiers, colorants, dyes, gel formers, salts, moisturizers, complex formers, viscosity regulators or light screening agents without being limited thereto. Furthermore all known styling- and conditioning polymers can be used in combination with the condensation polymers in order to obtain special effects.

As traditional polymers the above mentioned cationic, anionic, neutral, non-ionic and amphoteric polymers may be used which are included explicitly herein.

In order to obtain certain properties the hair care preparations may additionally comprise conditioning compounds on silicone basis such as polyalkylsiloxane, polyarylsiloxane, polyarylalkylsiloxane, silicone resins, polyethersiloxane or dimethicon copolyole (CTFA) and amino functionalized silicone compounds such as amodimethicone (CTFA), GP 4 Silicone Fluid® and GP 7100® (Genesee), Q2 8220® (Dow Corning), AFL 40® (Union Carbide) or polymers as disclosed in EP-B 852 488.

Other suitable ingredients comprise silicone propfpolymers having a polymeric silicone backbone and non-silicone containing side chains or a non silicone containing polymeric backbone and silicone side chains such as Luviflex® Silk or polymers disclosed in EP-B 852 488.

Preferred hair care preparations containing the condensation polymer are styling preparations such as hair-sprays and hair foams.

In a preferred embodiment these preparations comprise:
1. 0.1 to 10 wt. % of at least on condensation polymer
2. 20 to 99 wt. % water and/or alcohol
3. 0 to 70 wt. % of at least one propellant
4. 0 to 20 wt. % of customary additives Propellants for hair sprays or aerosol foams are typically used propellants. Preferred are mixtures of propane/butane, pentane, dimethylether, 1,1-difluoroethane (HFC-152a), carbon dioxide, nitrogen or compressed air.

A preferred preparation for aerosol foams comprise:
1. 0.1 to 10 wt. % of at least on condensation polymer
2. 55 to 99.8 wt. % water and/or alcohol
3. 5 to 20 wt. % of a propellant 4. 0.1 to 5 wt. % of an emulsifier
5. 0 to 10 wt. % of customary additives Emulsifiers for aerosol foams may be all conventionally used non-ionic, cationic, anionic or amphoteric emulsifier.

Examples of non-ionic emulsifiers comprise (INC)-nomenclature) Laureths, e.g. Laureth-4; Cetheths, e.g. Cetheth-1, polyethyleneglycolcetylether; cethearaths, e.g. cetheareth-25, polyglycolfattyacidglycerides, hydroxylated lecithins, lactyl esters of fatty acids, alkylpolyglycosides.

Examples of cationic emulsifiers are cetyldimethyl-2-hydroxyethylammonium-dihydrogenphosphate, cetyltrimoniumchloride, cetyltrimmoniumbromide, cocotrimoniummethylsulfate quaternium-1 to x (INCI).

Anionic emulsifiers can be selected from alkylsulfate, alkylethersulfate, alkylsulfonate, alkylarylsulfonate, alkylsuccinate, alkylsulfosuccinate, N-alkoylsarcosinate, acyltaurate, acylisethionate, alkylphosphate, alkyletherphosphate, alkylethercarboxylate, alpha-olefinesulfonate, especially the alkali-und earth alkali salts, e.g. sodium, potassium, magnesium, calcium, as well as ammonium- and triethanolaminesalts. The alkylethersulfate, alkyletherphosphate and alkylethercarboxylate may comprise between 1 to 10 ethyleneoxide or propyleneoxide units, preferably 1 to 3 ethyleneoxide-units per molecule.

Preferred hair care preparations comprise hair gels. Such hair gels comprise exemplary:
1. 0.1 to 20 wt. % preferably 1 to 10 wt. % of at least one condensation polymer
2. 0 to 10 wt. % of at least one carrier (solvent), selected from C2 to C5 alcohols, preferably ethanol
3. 0.01 to 5 wt. %, preferably 0.2 to 3 wt. % of at least one thickener
4. 0 to 50 wt. % of a propellant
5. 0 to 10 wt. %, preferably 0.1 to 3 wt. % of a styling polymer different to 1.), preferably a water soluble non-ionic polymer
6. 0-1 wt. % of at least one refatter, preferably selected from glycerine and glycerine derivatives
7. 0 to 30 wt. % of other customary additives e.g. a silicone component
8. water ad 100 wt. %

An exemplary styling gel can be comprised as follows:
1. 0.1 to 10 wt. % of a condensation polymer
2. 60 to 99.85 wt. % of water and/or alcohol
3. 0.05 to 10 wt. % of a gel former
4. 0.20 wt. % of other customary additives As gel formers all typically cosmetic gel formers can be used such as slightly cross linked polyacrylic acid e.g. Carbomer (INCI), cellulose derivatives, polysaccharides e.g. xanthan gum, capryl/caprin triglyceride, sodiumacrylate-copolymers, polyquaternium-32 (and) paraffinum liquidum (INCI), sodiumacrylate-copolymers (and) paraffinum liquidum (INCI) (and) PPG-1 trideceth-6, polyquaternium-37 (and) propyleneglycoldicapratdicarylate (and) PPG-1 trideceth-6, polyquaternium-7, polyquaternium-44.

Preferred hair care preparations are shampoo preparations comprising the condensation polymer as strengthening and/or conditioning agent.

Preferred shampoo preparations comprise:
1. 0.05 to 10 wt. % of a condensation polymer
2. 25 to 94.95 wt. % of water
3. 5 to 50 wt. % of tenside (surface active ingredient)
4. 0 to 5 wt. % of an additional conditioning agent
5. 0 to 10 wt. % other customary additives All typically used anionic, neutral, amphoteric or cationic tensides may be used within the shampoo preparations.

Exemplary anionic tensides comprise alkylsulfate, alkylethersulfate, alkylsulfonate, alkylarylsulfonate, alkylsuccinate, alkylsulfosuccinate, N-alkoylsarcosinate, acyltaurate, acylisethionate, alkylphosphate, alkyletherphosphate, alkylethercarboxylate, alpha-olefinesulfonate, especially the alkali-und earth alkali salts, e.g. sodium, potassium, magnesium, calcium, as well as ammonium- and triethanolaminesalts. The alkylethersulfate, alkyletherphosphate and alkylethercarboxylate may comprise between 1 to 10 ethyleneoxide or propyleneoxide units, preferably 1 to 3 ethyleneoxide-units per molecule.

Suitable are e.g. sodium laurylsulfate, ammonium lauryl sulfate, sodium laurylethersulfate, ammonium laurylethersulfate, sodium lauroylsarconisate, sodiumoleylsuccinate, ammonium laurylsulfosuccinate, sodium dodecylbenzolsulfonate, triethanolamidodecylbenzolsulfonate.

Suitable amphoteric tensides are e.g. alkylbetaine, alkylamidopropylbetaine, alkylsulfobetaine, alkylglycinate, alkylcarboxyglycinate, alkylamphoacetate or propionate, alkylamphodiacetate or dipropionate such as cocodimethylsulfopropylbetaine, laurylbetaine, cocamidopropylbetaine or sodium cocamphopropionate.

Examples of non ionic tensides are e.g. reaction products of aliphatic alcohols or alkylphenols with 6 to 20 C-Atoms of a linear or branched alkyl chain with ethyleneoxide and/or propyleneoxide. The amount of alkyleneoxide is about 6 to mole to one mol alkohol. Furthermore alkylaminoxide, mono- or dialkylalkanolamide, fatty esters of polyethyleneglycols, alkylpolyglycosides or sorbitanetherester are suitable for the incorporation of hair care preparations according to the invention.

Furthermore, the shampoo preparations may contain the usual cationic tensides such as quaternized ammonium compounds e.g. cetyltrimethylammoniumchloride or bromide (INCI: cetrimoniumchloride or bromide), hydroxyethylcetyldimoniumphosphate (INCI: Quaternium-44), Luviquat® Mono LS (INCI: Cocotrimoniummethosulfate), poly (oxy-1,2-ethanediyl), ((OctadecyInitrilio) tri-2,1-ethanediyl) tris(hydroxy)-phosphate (1:1) (Salt) (INCI Quaternium-52).

For special effects typical conditioning agents may be combined with the condensation polymers within the shampoo preparations such as the previously mentioned cationic polymers named polyquaternium (INCI), especially copolymers of vinylpyrrolidone/N-vinylimidazoliumsalts (Luviquat® FC, Luviquat® HM, Luviquat® MS, Luviquat® Ultracare), copolymers of N-vinylpyrrolidone/dimethylaminoethylmethacrylate quaternized with diethysulfate (Luviquat® PQ 11), copolymers of N-cationic cellulose derivatives (Polyquaternium-4 and -10), acrylamidecopolymers (Polyquaternium-7). Furthermore protein hydrolysates may be used as well as conditioning agents on silicone basis such as polyarylsiloxane, polyarylalkylsiloxane, polyethersiloxane or silicone resins. Other suitable silicone compounds are dimethicondopolyole (CTFA) and amino functionalised silicone derivatives such as amodimethicone (CTFA).

Furthermore cationic guar derivatives such as guarhydroxypropyltrimoniumchloride (INCI) may be used.

Preferred hair care compositions are hair treatment preparations such as rinse off- and leave on-conditioners comprising the condensation polymer as strengthening and/or conditioning agent.

Preferred conditioner preparations comprise:
1. 0.05-10 wt. % of a condensation polymer,
2. 25-94.95 wt. % of water;
3. 0.1-30 wt. % of tensides/emulsifier/surface active ingredient;

4. 0.1-30 wt. % of oil/emollient;
5. 0-5 wt. % of an additional conditioning agent;
6. 0-10 wt. % other customary additives.

All typically used anionic, neutral, amphoteric or cationic tensides may be used within the conditioner preparations.

Exemplary anionic tensides comprise alkylsulfate, alkylethersulfate, alkylsulfonate, alkylarylsulfonate, alkylsuccinate, alkylsulfosuccinate, N-alkoylsarkosinate, acyltaurate, acylisethionate, alkylphosphate, alkyletherphosphate, alkylethercarboxylate, alpha-olefinesulfonate, especially the alkali-und earth alkali salts, e.g. sodium, potassium, magnesium, calcium, as well as ammonium- and triethanol aminesalts. The alkylethersulfate, alkyletherphosphate and alkylethercarboxylate may comprise between 1 to 10 ethyleneoxide or propyleneoxide units, preferably 1 to 3 ethyleneoxide-units per molecule.

Suitable are e.g. sodium laurylsulfate, ammonium lauryl sulfate, sodium laurylethersulfate, ammonium laurylethersulfate, sodium lauroylsarkonisate, sod iumoleylsuccinate, ammonium laurylsulfosuccinate, sodium dodecylbenzolsulfonate, triethanolamidodecylbenzolsulfonate.

Suitable amphoteric tensides are e.g. alkylbetaine, alkylamidopropylbetaine, alkylsulfobetaine, alkylglycinate, alkylcarboxyglycinate, alkylamphoacetate or propionate, alkylamphodiacetate or dipropionate such as cocodimethylsulfopropylbetaine, laurylbetaine, cocamidopropylbetaine or sodium cocamphopropionate.

Examples of non ionic tensides are e.g. reaction products of aliphatic alcohols or alkylphenols with 6 to 20 C-Atoms of a linear or branched alkyl chain with ethyleneoxide and/or propyleneoxide. The amount of alkyleneoxide is about 6 to 60 mole to one mol alcohol. Furthermore alkylaminoxide, mono- or dialkylalkanolamide, fatty esters of polyethylene glycols, alkylpolyglycosides or sorbitanether ester are suitable for the incorporation of hair care compositions according to the invention.

Furthermore, the conditioner preparations may contain the usual cationic tensides such as quaternised ammonium compounds e.g. cetyltrimethylammoniumchloride or bromide (INCI: cetrimoniumchloride or bromide), hydroxyethylcetyldimonium phosphate (INCI: Quaternium-44), Luviquat® Mono LS (INCI: Cocotrimoniummethosulfate), poly (oxy-1,2-Ethandiyl), (OctadecyInitrilio) tri-2,1-Ethandiyl) tris-(hydroxy)-phosphate (INCI Quaternium-52).

For special effects typical conditioning agents may be combined with the condensation polymers within the conditioning preparations such as the previously mentioned cationic polymers named polyquaternium (INCI), especially copolymers of vinylpyrrolidone/N-vinylimidazoliumsalts (Luviquat® FC, Luviquat® HM, Luviquat® MS, Luviquat® Ultracare), copolymers of N-vinylpyrrolidone/dimethylaminoethylmethacrylate quaternised with diethylsulfate (Luviquat® PQ 11), copolymers of N-cationic cellulose derivatives (Polyquaternium-4 and -10), acrylamidcopolymers (Polyquaternium-7). Furthermore protein hydrolysates may be used as well as conditioning agents on silicone basis such as polyarylsiloxane, polyarylalkylsiloxane, polyethersiloxane or silicone resins. Other suitable silicone compounds are dimethicondopolyole (CTFA) and amino functionalised silicone derivatives such as amodimethicone (CTFA).

Furthermore cationic guar derivatives such as guarhydroxypropyltrimoniumchloride (INCI) may be used.

Furthermore, the conditioner preparations may contain the usual surface active ingredients like emulsifiers, solubilizers and the like. An emulsifier enables two or more immiscible components to be combined homogeneously. Moreover, the emulsifier acts to stabilize the composition. Emulsifiers that may be used in the present invention in order to form O/W, W/O, O/W/O or W/O/W emulsions/microemulsions include sorbitan oleate, sorbitan sesquioleate, sorbitan isostearate, sorbitan trioleate, polyglyceryl-3-diisostearate, polyglycerol esters of oleic/isostearic acid, polyglyceryl-6 hexaricinolate, polyglyceryl-4-oleate, polygylceryl-4 oleate/PEG-8 propylene glycol cocoate, oleamide DEA, TEA myristate, TEA stearate, magnesium stearate, sodium stearate, potassium laurate, potassium ricinoleate, sodium cocoate, sodium tallowate, potassium castorate, sodium oleate, and mixtures thereof. Further exemplary emulsifiers are phosphate esters and the salts thereof such as cetyl phosphate (Amphisol® A), diethanolamine cetyl phosphate (Amphisol®), potassium cetyl phosphate (Amphisol® K), sodium glyceryl oleate phosphate, hydrogenated vegetable glycerides phosphate and mixtures thereof. Furthermore, one or more synthetic polymers may be used as an emulsifier. For example, PVP eicosene copolymer, acrylates/$C_{10-30}$ alkyl acrylate crosspolymer, acrylates/steareth-20 methacrylate copolymer, PEG-22/dodecyl glycol copolymer, PEG-45/dodecyl glycol copolymer, and mixtures thereof. Further exemplary emulsifiers are fatty alcohols, e.g. cetearyl alcohol (Lanette O, Cognis Cooperation), cetyl alcohol (Lanette 16, Cognis Cooperation), stearyl alcohol (Lanette 18, Cognis Cooperation), Laneth-5 (Polychol 5, Croda Chemicals), furthermore sucrose and glucose derivatives, e.g. sucrose distearate (Crodesta F-10, Croda Chemicals), Methyl glucose isostearate (Isolan IS, Degussa Care Chemicals), furthermore ethoxylated carboxylic acids or polyethyleneglycol esters and polyethyleneglycol ethers, e.g. steareth-2 (Brij 72, Uniqema), steareth-21 (Brij 721, Uniqema), ceteareth-25 (Cremophor A25, BASF Cooperation), PEG-40 hydrogenated castor oil (Cremophor RH-40, BASF Cooperation), PEG-7 hydrogenated castor oil (Cremophor WO7, BASF Cooperation), PEG-30 Dipolyhydroxystearate (Arlacel P 135, Uniqema), furthermore glyceryl esters and polyglyceryl esters, e.g. polyglyceryl-3-diisostearate (Hostacerin TGI, Clariant Cooperation), polyglyceryl-2 dipolyhydroxystearate (Dehymuls PGPH, Cognis Cooperation), polyglyceryl-3 methylglucose distearate (Tego Care 450, Degussa Care Chemicals). The preferred emulsifiers are cetyl phosphate (Amphisol® A), diethanolamine cetyl phosphate (Amphisol®), potassium cetyl phosphate (Amphisol® K), PVP Eicosene copolymer, acrylates/$C_{10-30}$-alkyl acrylate crosspolymer, PEG-20 sorbitan isostearate, sorbitan isostearate, and mixtures thereof. The one or more emulsifiers are present in a total amount of at least 0.01 wt. % of the total weight of the composition. Preferably about 0.01 wt. % to about 20 wt. % of the total weight of the composition of the present invention is used. Most preferred, about 0.1 wt. % to about 10 wt. % of emulsifiers are used.

Furthermore, the conditioner preparations may contain the usual oily and fatty components may be chosen from mineral oils and mineral waxes; oils such as triglycerides of caprinic acid and/or caprylic acid or castor oil; oils or waxes and other natural or synthetic oils, in an preferred embodiment esters of fatty acids with alcohols e.g. isopropanol, propyleneglycol, glycerin or esters of fatty alcohols with carbonic acids or fatty acids; alkylbenzoates; and/or silicone oils.

Exemplary fatty substances which can be incorporated in the oil phase of the emulsion, microemulsion, oleo gel, hydrodispersion or lipodispersion of the present invention are advantageously chosen from esters of saturated and/or unsaturated, linear or branched alkyl carboxylic acids with 3 to 30 carbon atoms, and saturated and/or unsaturated, linear and/or branched alcohols with 3 to 30 carbon atoms as well as esters of aromatic carboxylic acids and of saturated and/or unsaturated, linear or branched alcohols of 3-30 carbon atoms. Such esters can advantageously be selected from octylpalmitate, octylcocoate, octylisostearate, octyldodecylmyristate, cetearylisononanoate, isopropylmyristate, isopropylpalmitate, isopropylstearate, isopropyloleate, n-butylstearate, n-hexyllaurate, n-decyloleate, isooctylstearate, isononylstearate, isononylisononanoate, 2-ethyl hexylpalmitate, 2-ethylhexyllaurate, 2-hexyldecylstearate, 2-octyldodecylpalmitate, stearylheptanoate, oleyloleate, oleylerucate, erucyloleate, erucylerucate, tridecylstearate, tridecyltrimellitate, as well as synthetic, half-synthetic or natural mixtures of such esters e.g. jojoba oil.

Other fatty components suitable for conditioner preparations of the present invention include polar oils such as lecithins and fatty acid triglycerides, namely triglycerol esters of saturated and/or unsaturated, straight or branched carboxylic acid with 8 to 24 carbon atoms, preferably of 12 to 18 carbonatoms whereas the fatty acid triglycerides are preferably chosen from synthetic, half synthetic or natural oils (e.g. cocoglyceride, olive oil, sun flower oil, soybean oil, peanut oil, rape seed oil, sweet almond oil, palm oil, coconut oil, castor oil, hydrogenated castor oil, wheat oil, grape seed oil, macadamia nut oil and others); apolar oils such as linear and/or branched hydrocarbons and waxes e.g. mineral oils, vaseline (petrolatum); paraffins, squalane and squalene, polyolefines, hydrogenated polyisobutenes and isohexadecanes, favored polyolefines are polydecenes; dialkyl ethers such as dicaprylylether; linear or cyclic silicone oils such as preferably cyclomethicone (octamethylcyclotetrasiloxane; cetyldimethicone, hexamethylcyclotrisiloxane, polydimethylsiloxane, poly(methylphenylsiloxane) and mixtures thereof.

Other fatty components which can advantageously be incorporated in conditioner preparations of the present invention are isoeikosane; neopentylglycoldiheptanoate; propyleneglycoldicaprylate/dicaprate; caprylic/capric/diglycerylsuccinate; butyleneglycol caprylat/caprat; $C_{12-13}$-alkyllactate; di-$C_{12-13}$-alkyltartrate; triisostearin; dipentaerythrityl hexacaprylat/hexacaprate; propyleneglycolmonoisostearate; tricaprylin; dimethylisosorbid. Especially beneficial is the use of mixtures $C_{12-15}$-alkylbenzoate and 2-ethylhexylisostearate, mixtures $C_{12-15}$-alkylbenzoate and isotridecylisononanoate as well as mixtures of $C_{12-15}$-alkylbenzoate, 2-ethylhexylisostearate and isotridecylisononanoate.

The oily phase of the conditioner preparation can also contain natural vegetable or animal waxes such as bees wax, china wax, bumblebee wax and other waxes of insects as well as shea butter and cocoa butter.

Suitable silicone oils are e.g. dimethylpolysiloxane, diethylpolysiloxane, diphenylpolysiloxane, cyclic siloxanes, poly (methylphenylsiloxanes) as well as amino-, fatty acid-, alcohol-, polyether-, epoxy-, fluoro-, glycoside-, and/or alkyl modified silicone compounds which are liquid or solid at room temperature and mixtures thereof. The number average molecular weight of the dimethicones and poly(methylphenylsiloxanes) is preferably in the range of 100 to 150000 g/mol. Preferred cyclic siloxanes comprise 4- to 8-membered rings which are for example commercially available as cyclomethicones.

In all preparations described above the sum of the ingredients adds to 100%.

The condensation polymers provided by the present invention are also suited for incorporation into home care and fabric care products, such as household cleansing and treatment agents, for example in laundry products and fabric softeners, non-detergent based fabric products, liquid cleansing and scouring agents, glass detergents, neutral cleaners (all-purpose cleaners), acid household cleaners (bath), bathroom cleaners, for instance in washing, rinsing and dishwashing agents, kitchen and oven cleaners, clear rinsing agents, dishwasher detergents, shoe polishes, polishing waxes, floor detergents and polishes, metal, glass and ceramic cleaners, textile-care products, rug cleaners and carpet shampoos, agents for removing rust, color and stains (stain remover salt), furniture and multipurpose polishes and leather and vinyl dressing agents (leather and vinyl sprays) air fresheners, drain cleaners, disinfectant solutions, upholstery cleaners, automotive care products (e.g., to clean and/or polish and protect paint, tires, chrome, vinyl, leather, fabric, rubber, plastic and fabric), degreasers, polishes (glass, wood, leather, plastic, marble, granite, and tile, etc.), and metal polishes and cleaners, candles, gel candles, air fresheners and fragrance oils (for the home).

Thus, the present invention also concerns home care and fabric care products containing condensation polymers in accordance with the invention such as particularly disclosed above.

The condensation polymers may be employed in fabric treatment that takes place after use of the fabric, referred to as fabric care. Such treatments include laundering, which uses detergents, laundry aids and/or fabric conditioner, and the application of non-detergent based fabric care products, such as spray-on products. When employed in this fashion, the condensation polymer is intended for deposition onto the fabric and used to protect the fabric, colorants and fragrances associated with said these fabrics from environmental damage.

In a further embodiment the invention relates to the use of an effective amount of a condensation polymer as defined above in protective, anti corrosion or decorative coatings; paper coating formulations; inks; biocides; oil field chemicals; and for the immobilization of heavy metals in soil, bitumen or concrete, without being limited thereto.

The following examples are provided to further illustrate the processes and compositions of the present invention. These examples are illustrative only and are not intended to limit the scope of the invention in any way.

EXAMPLE 1

Synthesis of a condensation polymer comprising a group (i) wherein a is ethylene, $R^1$ to $R^6$ are hydrogen, n, m, o=1 and $X^1$, $X^2$ and $X^3$ are hydroxy 355 g of tris(hydroxymethyl)aminomethane (TRIS) and 245 g of succinic anhydride were added to a glass reactor equipped with stirrer and condenser, and which can be heated by oil. The mixture was slowly heated to 180° C. and 2 h later vacuum was applied to remove the reaction water. After 5 h the mixture was cooled and a glassy polymer with an acid value of 2 mg KOH/g was obtained.

EXAMPLE 2

Synthesis of a condensation polymer comprising a group (i) wherein a is ethylene, $R^1$ to $R^6$ are hydrogen, n, m, o=1 and wherein at least one $X^1$, $X^2$ or $X^3$ is a group —O—CO—CH$_2$CH$_2$—CO—N($R^8$, $R^9$) wherein $R^8$ and $R^9$ form a N-methyl piperazine group 276 g of N-methyl piperazine was added to a glass reactor equipped with stirrer and condenser, and which can be heated by oil. Next 384 g succinic anhydride was added and the mixture was slowly heated to 120° C. 1 h after the start, 139 g TRIS was added and the mixture was heated to 180° C. After ½ h, vacuum was applied to remove the reaction water. After 12 h the mixture was cooled and a polymer with an acid value of 47 mg KOH/g was obtained.

EXAMPLE 3

Synthesis of a condensation polymer comprising a group (I) wherein A is 1,2-cyclohexyl, $R^1$ to $R^6$ are hydrogen, n, m, o=1 and wherein at least one $X^1$, $X^2$ or $X^3$ is a group —O—CO-(1,2-$C_6H_4$)—CO—N($R^8$,$R^9$) wherein $R^8$ and $R^9$ are dimethyl aminopropyl groups.

276 g of bis(N,N-dimethyl aminopropyl) amine and 295 g of molten hexahydro phthalic anhydride were added to a glass reactor equipped with stirrer and condenser, and which can be heated by oil. The mixture was slowly heated to 120° C. 1 h after the start, 80 g TRIS was added and the mixture was heated to 180° C. After ½ h, vacuum was applied to remove the reaction water. After 16 h the mixture was cooled and a polymer with an acid value of 25 mg KOH/g was obtained.

EXAMPLE 4

Synthesis of a condensation polymer comprising a group (i) wherein A is ethylene $R^1$ to $R^6$ are Hydrogen, n, m, o=1 and wherein at least one $X^1$, $X^2$ or $X^3$ is a group —O—CO—$CH_2CH_2$—$COOR^{10}$ wherein $R^{10}$ is a polyethyleneoxide group 407 g of polyethyleneoxide-monomethylether (MW=750) was added to a glass reactor equipped with stirrer and condenser, and which can be heated by oil. Next 68 g succinic anhydride was added and the mixture was slowly heated to 120° C. 1 h after the start, 25 g TRIS was added and the mixture was heated to 180° C. After ½ h, vacuum was applied to remove the reaction water. After 12 h the mixture was cooled and a polymer with an acid value of 14 mg KOH/g was obtained.

EXAMPLE 5

Synthesis of a condensation polymer comprising a group (I) wherein A is ethylene $R^1$ to $R^6$ are Hydrogen, n, m, o=1 and wherein $X^1$ is methyl and at least one $X^2$ or $X^3$ is a group —O—CO—$CH_2CH_2$—$COOR^{10}$ wherein $R^{10}$ is a polyethyleneoxide group 312 g of polyethyleneoxide-monomethylether (MW=750) was added to a glass reactor equipped with stirrer and condenser, and which can be heated by oil. Next 68 g succinic anhydride was added and the mixture was slowly heated to 120° C. 1 h after the start, 37 g 2-amino-2-ethyl-1,3-propanediol was added and the mixture was heated to 180° C. After ½ h vacuum was applied to remove the reaction water. After 12 h the mixture was cooled and a polymer with an acid value of 17 mg KOH/g was obtained.

EXAMPLE 6

Synthesis of a condensation polymer comprising a group (I) wherein at least one $X^1$, $X^2$ and $X^3$ is an imidazolino group.

246 g of TRIS, 170 g of succinic anhydride and 184 g imidazole were added to a glass reactor equipped with stirrer and condenser, and which can be heated by oil. The mixture was slowly heated to 180° C. and 2 h later vacuum was applied to remove the reaction water. After 5 h the mixture was cooled and a glassy polymer with an acid value of 10 mg KOH/g was obtained. The ratio of imidazolino end groups to hydroxy end groups in the condensation polymer is approx. 70 wt % to 30 wt. %.

EXAMPLE 7

Synthesis of a condensation polymer comprising a group (I) wherein A is ethylene and 1-dodecenylethylene (1:1), $R^1$ to $R^6$ are hydrogen, n, m, o=1 and wherein at least one $X^1$, $X^2$ or $X^3$ is a group —O—CO—$R^7$ wherein $R^7$ is derived from coconut fatty acid 183 g of dodecenyl succinic anhydride, 169 g of succinic anhydride, 141 g coconut fatty acid and 208 g of TRIS were added to a glass reactor equipped with stirrer and condenser, and which can be heated by oil. The mixture was slowly heated to 180° C. and 2 h later vacuum was applied to remove the reaction water. After 5 h the mixture was cooled and a polymer with an acid value of 9 mg KOH/g was obtained. The ratio of coconut fatty acid end groups to hydroxy end groups in the condensation polymer is approx. 25 wt. % to 75. wt %.

EXAMPLE 8

Synthesis of a condensation polymer comprising a group (I) wherein the N-methyl piperazine end groups are quaternized.

50 g of the polymer of example 2 was dissolved in 50 g water and at room temperature 24.2 g of dimethyl sulphate was slowly added. First the mixture was turbid but within 10 min the temperature raised to about 50° C. and the mixture became clear. After 24 h the fully quaternized polymer solution was ready for use.

EXAMPLE 9

Synthesis of a condensation polymer comprising a group (I) wherein the dimethyl aminopropyl end groups are quaternized.

50 g of the polymer of example 3 was dissolved in 50 g water and at room temperature 21.9 g of dimethyl sulphate was slowly added. First the mixture was turbid but within 10 min the temperature raised to about 50° C. and the mixture became clear. After 24 h the fully quaternized polymer solution was ready for use.

EXAMPLE 10

Synthesis of a condensation polymer comprising a group (I) wherein A is 1,2-cyclohexyl, $R^1$ to $R^6$ are hydrogen, n, m, o=1 and wherein at least one $X^1$, $X^2$ or $X^3$ is a group wherein at least one $X^1$, $X^2$ or $X^3$ is a group —O—CO—$R^7$ wherein $R^7$ is derived from sunflower fatty acid.

184 g of hexahydro phthalic anhydride, 106 g diisopropanol amine and 73 g of TRIS are added to a glass reactor equipped with stirrer and condenser, and which can be heated by oil. The mixture is slowly heated to 160° C. and next 336 g sunflower fatty acid is added, 2 h later vacuum is applied to remove the reaction water. After 5 h the mixture is cooled and a polymer with an acid value of 6 mg KOH/g is obtained.

EXAMPLE 11

| Hair styling spray | |
|---|---|
| INCI NOMENCLATURE | wt. % |
| Alcohol, anhydrous | ad 100 |
| Octylacrylamide/acrylate/butylaminoethylmethacrylate copolymer | 2.50 |

-continued

| Hair styling spray | |
|---|---|
| INCI NOMENCLATURE | wt. % |
| Hydroxypropyl cellulose | 0.50 |
| Aminomethylpropanol | 0.50 |
| Perfume oil | 0.200 |
| Condensation polymer according to the invention | 0.01-20 |

The hydroxypropyl cellulose is first dissolved in half of the alcohol and is subsequently charged with aminomethylpropanol. The other components, with exception of the acrylate resin, are dissolved in alcohol and this solution is added under agitation to the hydroxypropyl cellulose followed by the addition of the acrylate resin.

EXAMPLE 12

| Protective Styling Hair Mousse | |
|---|---|
| INCI NOMENCLATURE | wt. % |
| Aqua (water) | ad 100 |
| Polyquaternium-4 | 2.00 |
| Cocamidopropylamine Oxide | 0.40 |
| PEG-12 Dimethicone | 0.20 |
| Propylene Glycol & Diazolidinyl Urea & Methylparaben & Propylparaben | 1.00 |
| Perfume oil | 0.20 |
| Propane/Butane | 10.00 |
| Condensation polymer according to the invention | 0.01-20 |

Add the ingredients in the order shown under agitation. Afterwards, charge in adequate containers with propane/butane.

EXAMPLE 13

| Shampoo for greasy hair | |
|---|---|
| INCI NOMENCLATURE | wt. % |
| Sodium myreth sulfate | 50.00 |
| TEA abietoyl (?) collagen hydrolysate | 3.50 |
| Laureth-3 | 3.00 |
| Phosphonomethylchitosan sodium salt | 0.01 |
| Aqua (water) | ad 100 |
| Colorant (D&C Red No. 33) | 0.20 |
| Parfume oil | 0.15 |
| Condensation polymer according to the invention | 0.01-20 |

The components are mixed with stirring at RT until they are completely dissolved.

EXAMPLE 14

| Anti Dandruff Shampoo | |
|---|---|
| INCI NOMENCLATURE | wt. % |
| Aqua (water) | ad 100 |
| Ammonium laureth sulphate | 35.00 |

-continued

| Anti Dandruff Shampoo | |
|---|---|
| INCI NOMENCLATURE | wt. % |
| Ammonium lauryl sulphate | 15.00 |
| Glycol disearate | 1.00 |
| Dimethicone | 1.00 |
| Cetyl alcohol | 0.50 |
| Cocamide MEA | 3.00 |
| ZPT | 1.00 |
| Guar hydroxypropyltrimonium chloride | 0.20 |
| Hydrogenated polydecene | 1.00 |
| Polyquaternium 10 | 0.10 |
| PEG 7m | 0.50 |
| Trimethylpropane tricaprylate/tricaprate | 1.00 |
| Preservative | q.s. |
| Fragrance | 0.30 |
| E 104, E 110, E 132 | 0.02 |
| Condensation polymer according to the invention | 0.01-20 |

EXAMPLE 15

| Conditioner Shampoo | |
|---|---|
| INCI NOMENCLATURE | wt. % |
| Aqua (water) | ad 100 |
| Sodium laureth sulphate | 25.00 |
| Cocamidopropyl betaine | 5.00 |
| Sodium chloride | 2.50 |
| Glycol distearate | 1.00 |
| Glycerine | 2.00 |
| Dimethiconol | 0.50 |
| Fragrance | 0.50 |
| Coco-glucoside | 3.00 |
| Carbomer | 0.10 |
| Arginine | 0.05 |
| Glyceryl oleate | 0.05 |
| Glyceryl stearate | 1.00 |
| Guar hydroxypropyltrimonium chloride | 0.10 |
| Panthenol | 1.00 |
| Disodium EDTA | 0.05 |
| Preservative | q.s. |
| Hydrolyzed keratin | 0.10 |
| Citric acid/sodium hydroxide | q.s |
| Condensation polymer according to the invention | 0.01-20 |
| E 102, E 110, FD&C blue | 0.01 |

EXAMPLE 16

| Shampoo with plant extracts | |
|---|---|
| INCI NOMENCLATURE | wt. % |
| Aqua (water) | ad 100 |
| Sodium laureth sulfate | 25.00 |
| Lauryl glucoside | 10.00 |
| Cocamidopropyl betaine | 5.00 |
| Propylene glycol | 2.0 |
| Perfume oil | 1.25 |
| Sodium citrate | 0.25 |
| Sodium benzoate | 0.20 |
| Panthenol | 1.00 |
| Sodium formate | 0.20 |
| Polyquaternium-10 | 0.20 |
| Hydroxypropyl guar hydroxypropyltrimonium chloride | 0.05 |
| PEG-35 castor oil | 1.00 |
| Maris sal | 1.25 |

-continued

| Shampoo with plant extracts | |
|---|---|
| INCI NOMENCLATURE | wt. % |
| Polysorbate 20 | 1.00 |
| Tocopheryl acetate | 0.20 |
| *Prunus armeniaca* | 0.20 |
| *Echinacea purpurea* | 0.05 |
| Retinyl palmitate | 0.05 |
| Tocopherol | 0.05 |
| Linoleic acid | 0.20 |
| Preservative | 1.00 |
| Condensation polymer according to the invention | 0.01-20 |
| CI77891 | 0.02 |

EXAMPLE 17

| Shine Shampoo | |
|---|---|
| INCI NOMENCLATURE | wt. % |
| Aqua (water) | Ad 100 |
| Sodium laureth sulfate | 15.00 |
| Disodium cocoamphodiacetate | 15.00 |
| Sodium chloride | 2.00 |
| Glycol distearate | 1.00 |
| Cocamidopropyl PYL betaine | 2.00 |
| Laurdimonium hydroxypropyl hydrolyzed wheat protein | 1.00 |
| PEG-12 dimethicone | 1.00 |
| Guar hydroxypropyltrimonium chloride | 0.05 |
| Hydrolyzed wheat protein | 0.20 |
| Laureth-4 | 1.00 |
| PEG-7 glyceryl, cocoate | 2.00 |
| Hydrogenated castor oil | 1.00 |
| Laureth-2 | 0.50 |
| PEG-55 propylene glycol oleate | 2.00 |
| Propylene glycol | 2.00 |
| Mica | 0.20 |
| Citric acid | 0.01 |
| Fragrance | 1.00 |
| E 110, E 104, E 122 | 0.05 |
| Condensation polymer according to the invention | 0.01-20 |

EXAMPLE 18

| Shower gel | |
|---|---|
| INCI NOMENCLATURE | wt. % |
| Aqua (water) | Ad to 100 |
| Sodium Laureth Sulfate | 12.90 |
| Cocamidopropyl Betaine | 2.50 |
| Potassium Cocoyl Hydrolyzed Collagen | 1.50 |
| Sodium Chloride | 1.00 |
| Perfume oil | 1.00 |
| Hydrolyzed Collagen | 0.90 |
| Decyl Glucoside | 0.90 |
| Polyquaternium 10 | 0.20 |
| Propylene Glycol | 0.18 |
| 5-Bromo-5-Nitro-1,3-Dioxane | 0.02 |
| Chinoline yellow E 104 1% solution | 0.01 |
| Condensation polymer according to the invention | 0.01-20 |

EXAMPLE 19

| Make up/Foundation/Day Cream | | |
|---|---|---|
| | INCI NOMENCLATURE | wt. % |
| A) | Octyldodecanol | 4.00 |
| | Glyceryl Stearate SE | 4.50 |
| | Talc | 1.00 |
| | Titanium Dioxide | 6.00 |
| | Iron Oxides | 0.80 |
| | *Ricinus Communis* (Castor) Seed Oil | 8.00 |
| | Sorbitan Sesquioleate | 0.50 |
| | Steareth-2 | 0.50 |
| | Tocopheryl Acetate | 2.00 |
| | Disodium EDTA | 0.10 |
| | BHT | 0.05 |
| | Phenoxyethanol & Methylparaben & Ethylparaben & Butylparaben & Propylparaben & Isobutylparaben | 0.60 |
| | Condensation polymer according to the invention | 0.20 |
| | Potassium Cetyl Phosphate | 2.00 |
| B) | Aqua (water) | Ad 100 |
| | Propylene Glycol | 5.00 |
| | Carbomer | 1.00 |
| C) | Cyclomethicone | 4.00 |
| | Dimethicone | 5.00 |
| | Perfume oil | 0.20 |

Heat part A) to 85° C. while stirring. When homogeneous, add part B) pre-heated to 75° C. While mixing, cool to ambient temperature, (not above 25° C. and add part C) under stirring. Pass trough a 3-Rollmill.

EXAMPLE 20

| Green colored glass detergent | |
|---|---|
| INCI NOMENCLATURE | wt. % |
| Anionic/amphoteric surfactants (Lumurol RK) | 0.70 |
| Butyl glycol | 5.00 |
| Isopropanol | 20.00 |
| Colorant (D&C Green No. 2) | 0.05 |
| Aqua (water) | ad 100 |
| Perfume oil | 4.00 |
| Condensation polymer according to the invention | 0.01-20 |

The components are mixed with stirring at RT until a homogenous mixture is obtained.

EXAMPLE 21

| Nail varnish | |
|---|---|
| INCI NOMENCLATURE | wt. % |
| Methyl ethyl ketone | 36.00 |
| Isopropyl alcohol | 28.00 |
| Aqua (water) | ad 100 |
| Ethyl acetate | 20.00 |
| Tocopheryl acetate | 0.05 |
| Perfume oil | 0.50 |
| Condensation polymer according to the invention | 0.01-20 |
| CI 42090 | 0.01 |

The components are mixed with stirring at RT until a homogenous mixture is obtained. Excellent results are achieved.

EXAMPLE 22

| Conditioning Mousse | |
|---|---|
| INCI NOMENCLATURE | wt. % |
| Polyquaternium-11 | 5.00 |
| Condensation polymer according to the invention | 0.01-20 |
| Hydroxyethyl Cetyldimonium Phosphate | 0.50 |
| Alcohol | 10.00 |
| Perfume oil | 0.40 |
| Preservative | q.s. |
| Aqua (water) | 69.10 |
| Propane/Butane | 10.00 |

EXAMPLE 23

| Aerosol Spray VOC 80 | |
|---|---|
| INCI NOMENCLATURE | wt. % |
| Condensation polymer according to the invention | 0.01-20 |
| Acrylates Copolymer | 1.00 |
| Aminomethyl Propanol | 0.24 |
| Alcohol | 35.00 |
| Aqua (water) | Ad 100 |
| Cyclopentylsiloxane | 0.10 |
| Perfume oil | 0.10 |
| Butane | 10.00 |
| Dimethylether | 35.00 |

Add all ingredients and mix intensively until a homogeneous solution is obtained.

EXAMPLE 24

| Setting Lotion/Solution | |
|---|---|
| INCI NOMENCLATURE | wt. % |
| Condensation polymer according to the invention | 0.01-20 |
| PEG-8 | 0.20 |
| Perfume oil | 0.10 |
| Aqua (water) | 10.00 |
| Alcohol | Ad 100 |

Add all ingredients and mix intensively until a homogeneous solution is obtained.

EXAMPLE 25

| Hair Gel | |
|---|---|
| INCI NOMENCLATURE | wt. % |
| Carbomer | 0.50 |
| Aqua (water) | Ad 100 |

-continued

| Hair Gel | |
|---|---|
| INCI NOMENCLATURE | wt. % |
| Triethanolamine | 0.70 |
| Condensation polymer according to the invention | 0.01-20 |
| Acrylates/C1-2 Succinates/Hydroxyacrylates Copolymer | 2.00 |
| Aminomethyl Propanol | 0.19 |
| Perfume oil | q.s. |
| PEG-40 Hydrogenated Castor Oil | q.s. |
| PEG-8 | 0.10 |
| Phenoxyethanol, Methylparaben, Butylparaben, Ethylparaben and Propylparaben | 0.10 |
| Hydroxyethylcellulose | 0.50 |

Add all ingredients of part 1 and mix intensively until a homogeneous gel is obtained.

What is claimed is:

1. A hair care composition which comprises an effective hair care amount of a condensation polymer carrying at least two groups of the general formula (I)

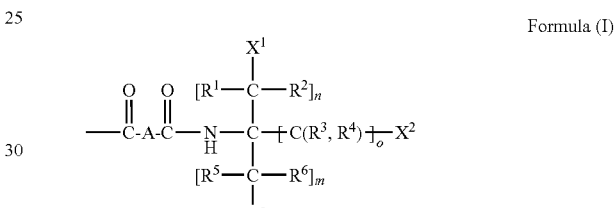

Formula (I)

wherein
the free bond extends to the polymer backbone;
A is an, optionally substituted, (C6-C24) aryldiradical or an, optionally substituted, (C2-C24) (cyclo)alkyldiradical,
R1 to R6 are, independently of each other, hydrogen, C1-20-alkyl, C3-7-cycloalkyl or C6-10-aryl;
X1, X2 and X3 are, independently of each other, hydrogen, hydroxy, C1-20-alkyl, C1-20-alkoxy, C3-7-cycloalkyl, C6-10-aryl or a group —O—CO—R7, —O—CO-A-CO—N(R8,R9), —O—CO-A-CO—OR10, or —NHet;
R7 is C1-20-alkyl, C3-7 cycloalkyl, C6-10-aryl;
R8 and R9 are, independently of each other, (C 1-20) -alkyl or (C 6-10) -aryl groups; or (C 1-20) -alkyl or (C 6-10) -aryl groups substituted by a group containing at least one hetero atom or
R8 and R9 together with the nitrogen atom to which they are attached form a 5 or 6 membered ring wherein optionally one or several C-atoms are replaced by —NH, —N—(C1-20) -alkyl, —N-aryl, —O— or —S—;
R10 is C1-20-alkyl, C3-7-cycloalkyl, or C6-10-aryl;
NHet is, independently of each other, a mono-, bi- or multicyclic nitrogen containing heterocyclyl group attached via a nitrogen atom to the polymer which may be aromatic or partly or completely hydrogenated and may contain additional heteroatoms such as nitrogen, oxygen or sulfur and which may optionally be substituted; and
n, m, o are, independently of each other, an integer of 1 to 4, preferably n, m and o are equal to 1;
provided that no more than one of X1, X2 and X3 is hydrogen, C1-20-alkyl, C3-7 -cycloalkyl, or C6-10-aryl;

and wherein nitrogen containing groups may be quaternized or protonated.

2. The hair care composition as in claim 1, wherein at least one group of the general formula (I) of the condensation polymer is present, and wherein R1 to R6 are hydrogen.

3. The hair care composition as in claim 1, wherein one of X1, X2 and X3 is methyl.

4. The hair care composition as in claim 1, wherein in the condensation polymer at least one group of the general formula (I) is present wherein at least one of X1, X2 and X3 are hydroxy.

5. The hair care composition as in claim 1, wherein in the condensation polymer at least one group of the general formula (I) is present wherein at least one of X1, X2 and X3 is —O—CO—R7.

6. The hair care composition as in claim 5, wherein R7 is C1-20-alkyl.

7. The hair care composition as in claim 1, wherein in the condensation polymer at least one group of the general formula (I) is present wherein at least one of X1, X2 and X3 is —O—CO-A-CO—N(R8,R9).

8. The hair care composition as in claim 7, wherein R8 and R9 are di-(C1-20-alkyl)amino-C1-20-alkyl groups.

9. The hair care composition as in claim 7, wherein —N(R8,R9) is a 5- or 6-membered N-heterocyclic ring.

10. The hair care composition as in claim 9, wherein the 5- or 6- membered N-heterocyclic ring is N-methyl piperazino or morpholine group.

11. The hair care composition as in claim 1, wherein in the condensation polymer at least one group of the general formula (I) is present wherein at least one of X1, X2 and X3 is —O—CO-A-CO—OR10.

12. The hair care composition as in claim 11, wherein R10 is polyethyleneoxide, polypropyleneoxide methyl ether and/or polytetrahydrofurane.

13. The hair care composition as in claim 1, wherein in the condensation polymer at least one group of the general formula (I) is present wherein at least one of X1, X2 and X3 is —NHet.

14. The hair care composition as in claim 13, wherein —NHet is, independently of each other, a mono-, bi- or multicyclic nitrogen containing heterocyclyl group attached via a nitrogen atom to the polymer which may be aromatic or partly or completely hydrogenated and may contain additional heteroatoms such as nitrogen, oxygen or sulfur and which may optionally be substituted.

15. The hair care composition as in claim 14, wherein —NHet is a imidazolino group.

16. The hair care composition as in claim 1, wherein the condensation polymer is a polycondensation reaction product of a compound of the general formula (II)

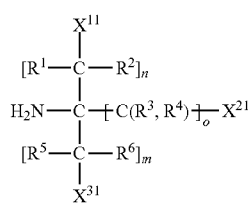

formula (II)

wherein R1 to R6 and n, m and o are as defined earlier in formula (I) and X11, X21 and X31 have the same meaning as X1, X2 and X3 in formula (I) as defined earlier, provided that at least one of X11, X21 and X31 is hydroxy, and further provided that no more than one of X11, X21 and X31 is hydrogen, C1-20-alkyl, C3-7-cycloalkyl, or C6-10-aryl;

with a dicarboxylic acid of the general formula

or the cyclic anhydride thereof wherein A has the same meaning as in formula (I) as defined earlier; and, optionally,
an acid of the general formula

and/ or a dialkylamine of the general formula

and/ or an alcohol of the general formula

and/ or a heterocycle of the general formula

wherein R7, R8, R9, R10 and —NHet have the same meaning as in formula (I) defined earlier and optionally, quaternization or protonation of a nitrogen group contained in the condensation polymer obtained.

17. The hair care composition as in claim 16, wherein the condensation polymer is the polycondensation reaction product of compounds of formula (II) with a compound of the formula (III) or the cyclic anhydride thereof with at least one additional alkanolamine according to formula (VIII):

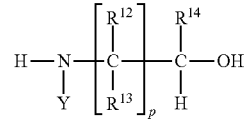

formula VIII in which:
Y is

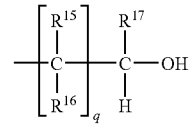

or a linear, branched or cyclic (C1-C20) alkyl group;
R12, R13, R14, R15, R16 and R17 are, independently of each other a hydrogen atom, (C6-C10) aryl groups, (C1-C8) alkyl groups or CH2OH
and p and q are an integer from 1 to 4, preferably, p and q are 1 is used in the polycondensation process.

18. The hair care composition according to claim 1, wherein the condensation polymer has a weight average molecular mass between 600 g/mol to 50,000 g/mol.

19. The hair care composition according to claim 1, wherein the average number of end groups X1, X2 and/or X3 per molecule of condensation polymer is between 2 and 250.

20. The hair care composition as in claim 5, wherein R7 is 2-ethylhexyl.

21. The hair care composition according to claim 1, wherein the condensation polymer has a weight average molecular mass between 800 g/mol and 25,000 g/mol.

22. The hair care composition according to claim 1, wherein the average number of end groups X1, X2 and/or X3 per molecule of condensation polymer is between 3 and 50.

* * * * *